United States Patent
Seemann et al.

(10) Patent No.: US 8,828,937 B2
(45) Date of Patent: Sep. 9, 2014

(54) BONE MORPHOGENETIC PROTEIN 2 (BMP2) VARIANTS WITH REDUCED BMP ANTAGONIST SENSITIVITY

(75) Inventors: Petra Seemann, Berlin (DE); Stefan Mundlos, Kleinmachnow (DE); Carsten Reissner, Muenster (DE); Georg Duda, Berlin (DE); Julia Zimmer, Berlin (DE)

(73) Assignee: Haase Investments UG, Alfeld (Leine) (DE)

( * ) Notice: Subject to any disclaimer, the term of this patent is extended or adjusted under 35 U.S.C. 154(b) by 31 days.

(21) Appl. No.: 13/255,909

(22) PCT Filed: Mar. 11, 2010

(86) PCT No.: PCT/EP2010/053103
§ 371 (c)(1),
(2), (4) Date: Nov. 23, 2011

(87) PCT Pub. No.: WO2010/103070
PCT Pub. Date: Sep. 16, 2010

(65) Prior Publication Data
US 2012/0058944 A1    Mar. 8, 2012

(30) Foreign Application Priority Data
Mar. 12, 2009 (EP) .................................. 09155049

(51) Int. Cl.
| | | |
|---|---|---|
| *A61K 38/18* | (2006.01) | |
| *C07K 14/435* | (2006.01) | |
| *C07K 14/46* | (2006.01) | |
| *C07K 14/465* | (2006.01) | |
| *C07K 14/51* | (2006.01) | |
| *C12N 15/00* | (2006.01) | |
| *C12N 15/12* | (2006.01) | |
| *C12N 15/63* | (2006.01) | |

(52) U.S. Cl.
USPC ......... 514/8.8; 514/15.4; 514/16.7; 514/16.8; 514/16.9; 514/17.1; 514/17.7; 514/21.2; 530/350; 536/23.1; 536/23.5; 435/69.1; 435/325; 435/252.3

(58) Field of Classification Search
None
See application file for complete search history.

(56) References Cited

U.S. PATENT DOCUMENTS

| | | | | |
|---|---|---|---|---|
| 5,393,739 A * | 2/1995 | Bentz et al. | ................... | 514/8.8 |
| 5,453,419 A * | 9/1995 | Murakami et al. | ............. | 514/8.8 |
| 5,645,084 A * | 7/1997 | McKay | ........................ | 128/898 |
| 6,333,312 B1 * | 12/2001 | Kuberasampath et al. | .... | 514/8.8 |
| 6,861,404 B1 * | 3/2005 | Cohen et al. | ................... | 514/6.9 |
| 7,194,056 B2 * | 3/2007 | Kim et al. | ..................... | 375/371 |
| 7,524,817 B2 * | 4/2009 | Cohen et al. | ................... | 514/1.1 |
| 7,824,670 B2 * | 11/2010 | Haggiag et al. | ............. | 424/93.7 |
| 7,825,098 B2 * | 11/2010 | Kahn et al. | .................. | 514/44 R |
| 8,062,632 B2 * | 11/2011 | Lee et al. | ..................... | 424/93.1 |
| 2005/0106144 A1 * | 5/2005 | Luyten et al. | ............. | 424/145.1 |

FOREIGN PATENT DOCUMENTS

WO    01/92298 A2    12/2001

OTHER PUBLICATIONS

Ristevski (2005, Molecular Biotechnology 29:153-163).*
Smith (2002, J. Biotechnol. 99:1-22).*
Vukicevic et al. (1996, PNAS USA 93:9021-9026).*
Shen et al. (2004, Eur. J. Neurosci. 20:2031-2037).*
Wells, 1990, Biochemistry 29:8509-8517.*
Ngo et al., 1994, Merz et al., eds., The Protein Folding Problem and Tertiary Structure Prediction, Birkhauser, Boston, pp. 492-495.*
Tokuriki et al., 2009, Curr. Opin. Struc. Biol. 19:596-604.*
Phillips, A., J Pharm Pharmacology 53:1169-1174, 2001.*
Vidal et al. European Journal of Cancer. 41 : 2812-2818, 2005.*
Kirsch Thomas et al: "BMP-2 antagonists emerge from alterations in the low-affinity binding epitope for receptor BMPR-II" in: EMBO (European Molecular Biology Organization) Journal, vol. 19, No. 13, Jul. 3, 2000, pp. 3314-3324.

* cited by examiner

*Primary Examiner* — Elizabeth C Kemmerer
(74) *Attorney, Agent, or Firm* — Joyce von Natzmer; Agris & von Natzmer LLP

(57) ABSTRACT

The present invention is directed to an isolated peptide comprising or consisting of an amino acid sequence with an amino acid identity of at least 90% compared to mature human BMP2 with SEQ ID No. 1, characterized in that said amino acid sequence comprises at least two amino acid substitutions characterized in that a first amino acid substitution occurs at a position corresponding to N59, S88, E94, V99, K101 and/or N102 of SEQ ID No. 1 and to uses thereof.

23 Claims, 12 Drawing Sheets

Figure 1:
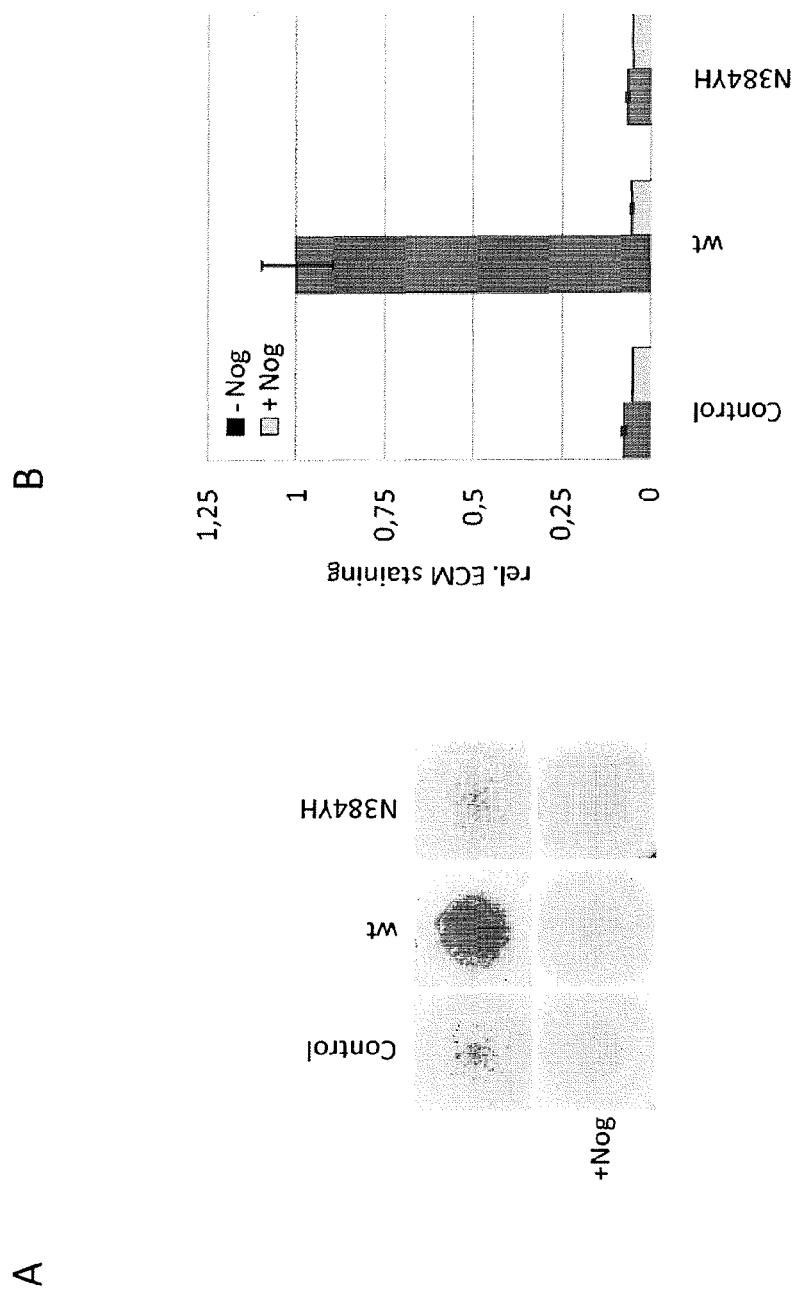

SEQUENCE LISTING

```
<160> NUMBER OF SEQ ID NOS: 31

<210> SEQ ID NO 1
<211> LENGTH: 114
<212> TYPE: PRT
<213> ORGANISM: homo sapiens

<400> SEQUENCE: 1

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
            85                  90                  95

Lys Val Val Leu Lys Asn Tyr Gln Asp Met Val Val Glu Gly Cys Gly
            100                 105                 110

Cys Arg

<210> SEQ ID NO 2
<211> LENGTH: 114
<212> TYPE: PRT
<213> ORGANISM: artificial
<220> FEATURE:
<223> OTHER INFORMATION: isolated peptide of the invention

<400> SEQUENCE: 2

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Lys His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
```

```
                        85                  90                  95

Lys Val Thr Leu Lys Asn Tyr Gln Asp Met Val Val Glu Gly Cys Gly
                100                 105                 110

Cys Arg

<210> SEQ ID NO 3
<211> LENGTH: 115
<212> TYPE: PRT
<213> ORGANISM: artificial
<220> FEATURE:
<223> OTHER INFORMATION: isolated peptide of the invention

<400> SEQUENCE: 3

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
                20                  25                  30

Val Ala Pro Pro Gly Tyr His Ala Phe Tyr Cys His Gly Glu Cys Pro
            35                  40                  45

Phe Pro Leu Ala Asp His Leu Asn Ser Thr Lys His Ala Ile Val Gln
        50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Tyr His Tyr Gln Asp Met Val Val Glu Gly Cys
                100                 105                 110

Gly Cys Arg
        115

<210> SEQ ID NO 4
<211> LENGTH: 114
<212> TYPE: PRT
<213> ORGANISM: artificial
<220> FEATURE:
<223> OTHER INFORMATION: isolated peptide of the invention

<400> SEQUENCE: 4

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
                20                  25                  30

Val Ala Pro Pro Gly Tyr His Ala Phe Tyr Cys His Gly Glu Cys Pro
            35                  40                  45

Phe Pro Leu Ala Asp His Leu Asn Ser Thr Thr His Ala Ile Val Gln
        50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Thr Leu Lys Asn Tyr Gln Asp Met Val Val Glu Gly Cys Gly
                100                 105                 110

Cys Arg

<210> SEQ ID NO 5
<211> LENGTH: 115
<212> TYPE: PRT
<213> ORGANISM: artificial
```

```
<220> FEATURE:
<223> OTHER INFORMATION: isolated peptide of the invention

<400> SEQUENCE: 5

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Thr His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Tyr His Tyr Gln Asp Met Val Val Glu Gly Cys
            100                 105                 110

Gly Cys Arg
        115

<210> SEQ ID NO 6
<211> LENGTH: 115
<212> TYPE: PRT
<213> ORGANISM: artificial
<220> FEATURE:
<223> OTHER INFORMATION: isolated peptide of the invention

<400> SEQUENCE: 6

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Thr Leu Lys Tyr His Tyr Gln Asp Met Val Val Glu Gly Cys
            100                 105                 110

Gly Cys Arg
        115

<210> SEQ ID NO 7
<211> LENGTH: 114
<212> TYPE: PRT
<213> ORGANISM: artificial
<220> FEATURE:
<223> OTHER INFORMATION: isolated peptides of the invention

<400> SEQUENCE: 7

Gln Ala Lys His Lys Gln Arg Lys Arg Leu Lys Ser Ser Cys Lys Arg
1               5                   10                  15

His Pro Leu Tyr Val Asp Phe Glu Asp Val Gly Trp Asn Asp Trp Ile
            20                  25                  30
```

Val Ala Pro Gly Tyr His Ala Phe Tyr Cys His Gly Glu Cys Pro
            35                  40                  45

Phe Pro Leu Ala Asp His Leu Asn Ser Thr Thr His Ala Ile Val Gln
 50                  55                  60

Thr Leu Val Asn Ser Val Asn Ser Lys Ile Pro Lys Ala Cys Cys Val
 65                  70                  75                  80

Pro Thr Glu Leu Ser Ala Ile Ser Met Leu Tyr Leu Asp Glu Asn Glu
                 85                  90                  95

Lys Val Val Leu Lys Asn Tyr Gln Asp Met Val Val Glu Gly Cys Gly
            100                 105                 110

Cys Arg

<210> SEQ ID NO 8
<211> LENGTH: 114
<212> TYPE: PRT
<213> ORGANISM: artificial
<220> FEATURE:
<223> OTHER INFORMATION: isolated peptide of the invention

<400> SEQUENCE: 8

Gln Ala Lys His Lys Gln Arg Lys Arg Leu Lys Ser Ser Cys Lys Arg
 1               5                  10                  15

His Pro Leu Tyr Val Asp Phe Ser Asp Val Gly Trp Asn Asp Trp Ile
            20                  25                  30

Val Ala Pro Lys Gly Tyr His Ala Phe Tyr Cys His Gly Glu Cys Pro
            35                  40                  45

Phe Pro Leu Ala Asp His Leu Asn Ser Thr Lys His Ala Ile Val Gln
 50                  55                  60

Thr Leu Val Asn Ser Val Asn Ser Lys Ile Pro Lys Ala Cys Cys Val
 65                  70                  75                  80

Pro Thr Glu Leu Ser Ala Ile Ser Met Leu Tyr Leu Asp Glu Asn Glu
                 85                  90                  95

Lys Val Val Leu Lys Asn Tyr Gln Asp Met Val Val Glu Gly Cys Gly
            100                 105                 110

Cys Arg

<210> SEQ ID NO 9
<211> LENGTH: 115
<212> TYPE: PRT
<213> ORGANISM: artificial
<220> FEATURE:
<223> OTHER INFORMATION: isolated peptide of the invention

<400> SEQUENCE: 9

Gln Ala Lys His Lys Gln Arg Lys Arg Leu Lys Ser Ser Cys Lys Arg
 1               5                  10                  15

His Pro Leu Tyr Val Asp Phe Glu Asp Val Gly Trp Asn Asp Trp Ile
            20                  25                  30

Val Ala Pro Pro Gly Tyr His Ala Phe Tyr Cys His Gly Glu Cys Pro
            35                  40                  45

Phe Pro Leu Ala Asp His Leu Asn Ser Thr Lys His Ala Ile Val Gln
 50                  55                  60

Thr Leu Val Asn Ser Val Asn Ser Lys Ile Pro Lys Ala Cys Cys Val
 65                  70                  75                  80

Pro Thr Glu Leu Ser Ala Ile Ser Met Leu Tyr Leu Asp Glu Asn Glu
                 85                  90                  95

Lys Val Val Leu Lys Tyr His Tyr Gln Asp Met Val Val Glu Gly Cys

```
                100             105             110
Gly Cys Arg
        115

<210> SEQ ID NO 10
<211> LENGTH: 282
<212> TYPE: PRT
<213> ORGANISM: homo sapiens

<400> SEQUENCE: 10

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg
        275                 280

<210> SEQ ID NO 11
<211> LENGTH: 396
<212> TYPE: PRT
<213> ORGANISM: homo sapiens

<400> SEQUENCE: 11

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
```

```
                    20                  25                  30
            Phe Ala Ala Ser Ser Gly Arg Pro Ser Ser Gln Pro Ser Asp Glu
                    35                  40                  45
            Val Leu Ser Glu Phe Glu Leu Arg Leu Ser Met Phe Gly Leu Lys
             50                  55                  60
            Gln Arg Pro Thr Pro Ser Arg Asp Ala Val Val Pro Tyr Met Leu
             65                  70                  75                  80
            Asp Leu Tyr Arg Arg His Ser Gly Gln Pro Gly Ser Pro Ala Pro Asp
                            85                  90                  95
            His Arg Leu Glu Arg Ala Ala Ser Arg Ala Asn Thr Val Arg Ser Phe
                    100                 105                 110
            His His Glu Glu Ser Leu Glu Glu Leu Pro Glu Thr Ser Gly Lys Thr
                    115                 120                 125
            Thr Arg Arg Phe Phe Phe Asn Leu Ser Ser Ile Pro Thr Glu Glu Phe
                    130                 135                 140
            Ile Thr Ser Ala Glu Leu Gln Val Phe Arg Glu Gln Met Gln Asp Ala
            145                 150                 155                 160
            Leu Gly Asn Asn Ser Ser Phe His His Arg Ile Asn Ile Tyr Glu Ile
                            165                 170                 175
            Ile Lys Pro Ala Thr Ala Asn Ser Lys Phe Pro Val Thr Arg Leu Leu
                    180                 185                 190
            Asp Thr Arg Leu Val Asn Gln Asn Ala Ser Arg Trp Glu Ser Phe Asp
                    195                 200                 205
            Val Thr Pro Ala Val Met Arg Trp Thr Ala Gln Gly His Ala Asn His
                    210                 215                 220
            Gly Phe Val Val Glu Val Ala His Leu Glu Glu Lys Gln Gly Val Ser
            225                 230                 235                 240
            Lys Arg His Val Arg Ile Ser Arg Ser Leu His Gln Asp Glu His Ser
                            245                 250                 255
            Trp Ser Gln Ile Arg Pro Leu Leu Val Thr Phe Gly His Asp Gly Lys
                    260                 265                 270
            Gly His Pro Leu His Lys Arg Glu Lys Arg Gln Ala Lys His Lys Gln
                    275                 280                 285
            Arg Lys Arg Leu Lys Ser Ser Cys Lys Arg His Pro Leu Tyr Val Asp
                    290                 295                 300
            Phe Ser Asp Val Gly Trp Asn Asp Trp Ile Val Ala Pro Pro Gly Tyr
            305                 310                 315                 320
            His Ala Phe Tyr Cys His Gly Glu Cys Pro Phe Pro Leu Ala Asp His
                            325                 330                 335
            Leu Asn Ser Thr Asn His Ala Ile Val Gln Thr Leu Val Asn Ser Val
                    340                 345                 350
            Asn Ser Lys Ile Pro Lys Ala Cys Cys Val Pro Thr Glu Leu Ser Ala
                    355                 360                 365
            Ile Ser Met Leu Tyr Leu Asp Glu Asn Glu Lys Val Val Leu Lys Asn
                    370                 375                 380
            Tyr Gln Asp Met Val Val Glu Gly Cys Gly Cys Arg
            385                 390                 395

<210> SEQ ID NO 12
<211> LENGTH: 396
<212> TYPE: PRT
<213> ORGANISM: artificial
<220> FEATURE:
<223> OTHER INFORMATION: isolated peptide of the invention
```

<400> SEQUENCE: 12

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Ser Met Phe Gly Leu Lys
    50                  55                  60

Gln Arg Pro Thr Pro Ser Arg Asp Ala Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Lys His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Thr Leu Lys Asn
    370                 375                 380

Tyr Gln Asp Met Val Val Glu Gly Cys Gly Cys Arg
385                 390                 395
```

<210> SEQ ID NO 13

<211> LENGTH: 397
<212> TYPE: PRT
<213> ORGANISM: artificial
<220> FEATURE:
<223> OTHER INFORMATION: isolated peptide of the invention

<400> SEQUENCE: 13

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Lys His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Tyr
370                 375                 380
```

```
His Tyr Gln Asp Met Val Val Glu Gly Cys Gly Cys Arg
385                 390                 395
```

```
<210> SEQ ID NO 14
<211> LENGTH: 396
<212> TYPE: PRT
<213> ORGANISM: artificial
<220> FEATURE:
<223> OTHER INFORMATION: isolated peptide of the invention

<400> SEQUENCE: 14

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Thr His Ala Ile Val Gln Thr Leu Val Asn Ser Val
            340                 345                 350
```

```
Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Thr Leu Lys Asn
370                 375                 380

Tyr Gln Asp Met Val Val Glu Gly Cys Gly Cys Arg
385                 390                 395

<210> SEQ ID NO 15
<211> LENGTH: 397
<212> TYPE: PRT
<213> ORGANISM: artificial
<220> FEATURE:
<223> OTHER INFORMATION: isloated peptide of the invention

<400> SEQUENCE: 15

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
290                 295                 300

Phe Ser Asp Val Gly Trp Asn Asp Trp Ile Val Ala Pro Pro Gly Tyr
305                 310                 315                 320
```

-continued

His Ala Phe Tyr Cys His Gly Glu Cys Pro Phe Pro Leu Ala Asp His
            325                 330                 335

Leu Asn Ser Thr Thr His Ala Ile Val Gln Thr Leu Val Asn Ser Val
            340                 345                 350

Asn Ser Lys Ile Pro Lys Ala Cys Cys Val Pro Thr Glu Leu Ser Ala
            355                 360                 365

Ile Ser Met Leu Tyr Leu Asp Glu Asn Glu Lys Val Val Leu Lys Tyr
            370                 375                 380

His Tyr Gln Asp Met Val Val Glu Gly Cys Gly Cys Arg
385                 390                 395

<210> SEQ ID NO 16
<211> LENGTH: 397
<212> TYPE: PRT
<213> ORGANISM: artificial
<220> FEATURE:
<223> OTHER INFORMATION: isolated peptide of the invention

<400> SEQUENCE: 16

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

```
Arg Lys Arg Leu Lys Ser Ser Cys Lys Arg His Pro Leu Tyr Val Asp
        290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Thr Leu Lys Tyr
370                 375                 380

His Tyr Gln Asp Met Val Val Glu Gly Cys Gly Cys Arg
385                 390                 395

<210> SEQ ID NO 17
<211> LENGTH: 396
<212> TYPE: PRT
<213> ORGANISM: artificial
<220> FEATURE:
<223> OTHER INFORMATION: isolated peptide of the invention

<400> SEQUENCE: 17

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
            85                  90                  95

His Arg Leu Glu Arg Ala Ala Ser Arg Ala Asn Thr Val Arg Ser Phe
        100                 105                 110

His His Glu Glu Ser Leu Glu Glu Leu Pro Glu Thr Ser Gly Lys Thr
    115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
            165                 170                 175

Ile Lys Pro Ala Thr Ala Asn Ser Lys Phe Pro Val Thr Arg Leu Leu
        180                 185                 190

Asp Thr Arg Leu Val Asn Gln Asn Ala Ser Arg Trp Glu Ser Phe Asp
    195                 200                 205

Val Thr Pro Ala Val Met Arg Trp Thr Ala Gln Gly His Ala Asn His
210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
            245                 250                 255
```

```
Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
            275                 280                 285

Arg Lys Arg Leu Lys Ser Ser Cys Lys Arg His Pro Leu Tyr Val Asp
290                 295                 300

Phe Glu Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
            325                 330                 335

Leu Asn Ser Thr Thr His Ala Ile Val Gln Thr Leu Val Asn Ser Val
            340                 345                 350

Asn Ser Lys Ile Pro Lys Ala Cys Cys Val Pro Thr Glu Leu Ser Ala
            355                 360                 365

Ile Ser Met Leu Tyr Leu Asp Glu Asn Glu Lys Val Val Leu Lys Asn
            370                 375                 380

Tyr Gln Asp Met Val Val Glu Gly Cys Gly Cys Arg
385                 390                 395

<210> SEQ ID NO 18
<211> LENGTH: 396
<212> TYPE: PRT
<213> ORGANISM: artificial
<220> FEATURE:
<223> OTHER INFORMATION: isolated peptide of the invention

<400> SEQUENCE: 18

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
            35                  40                  45

Val Leu Ser Glu Phe Glu Leu Arg Leu Leu Ser Met Phe Gly Leu Lys
50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
            85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
            115                 120                 125

Thr Arg Arg Phe Phe Phe Asn Leu Ser Ser Ile Pro Thr Glu Glu Phe
            130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
            165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
            195                 200                 205

Val Thr Pro Ala Val Met Arg Trp Thr Ala Gln Gly His Ala Asn His
210                 215                 220
```

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
            245                 250                 255

Trp Ser Gln Ile Arg Pro Leu Leu Val Thr Phe Gly His Asp Gly Lys
        260                 265                 270

Gly His Pro Leu His Lys Arg Glu Lys Arg Gln Ala Lys His Lys Gln
    275                 280                 285

Arg Lys Arg Leu Lys Ser Ser Cys Lys Arg His Pro Leu Tyr Val Asp
290                 295                 300

Phe Ser Asp Val Gly Trp Asn Asp Trp Ile Val Ala Pro Lys Gly Tyr
305                 310                 315                 320

His Ala Phe Tyr Cys His Gly Glu Cys Pro Phe Pro Leu Ala Asp His
            325                 330                 335

Leu Asn Ser Thr Lys His Ala Ile Val Gln Thr Leu Val Asn Ser Val
        340                 345                 350

Asn Ser Lys Ile Pro Lys Ala Cys Cys Val Pro Thr Glu Leu Ser Ala
    355                 360                 365

Ile Ser Met Leu Tyr Leu Asp Glu Asn Glu Lys Val Val Leu Lys Asn
370                 375                 380

Tyr Gln Asp Met Val Val Glu Gly Cys Gly Cys Arg
385                 390                 395

<210> SEQ ID NO 19
<211> LENGTH: 397
<212> TYPE: PRT
<213> ORGANISM: artificial
<220> FEATURE:
<223> OTHER INFORMATION: isolated peptide of the invention

<400> SEQUENCE: 19

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
            85                  90                  95

His Arg Leu Glu Arg Ala Ala Ser Arg Ala Asn Thr Val Arg Ser Phe
        100                 105                 110

His His Glu Glu Ser Leu Glu Glu Leu Pro Glu Thr Ser Gly Lys Thr
    115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
            165                 170                 175

Ile Lys Pro Ala Thr Ala Asn Ser Lys Phe Pro Val Thr Arg Leu Leu
        180                 185                 190

```
Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
                260                 265                 270

Gly His Pro Leu His Lys Arg Glu Lys Arg Gln Ala Lys His Lys Gln
                275                 280                 285

Arg Lys Arg Leu Lys Ser Ser Cys Lys Arg His Pro Leu Tyr Val Asp
290                 295                 300

Phe Glu Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Lys His Ala Ile Val Gln Thr Leu Val Asn Ser Val
                340                 345                 350

Asn Ser Lys Ile Pro Lys Ala Cys Cys Val Pro Thr Glu Leu Ser Ala
                355                 360                 365

Ile Ser Met Leu Tyr Leu Asp Glu Asn Glu Lys Val Val Leu Lys Tyr
                370                 375                 380

His Tyr Gln Asp Met Val Val Glu Gly Cys Gly Cys Arg
385                 390                 395
```

<210> SEQ ID NO 20
<211> LENGTH: 57
<212> TYPE: DNA
<213> ORGANISM: artificial
<220> FEATURE:
<223> OTHER INFORMATION: primer

<400> SEQUENCE: 20
ctgtaccttg acgagaatga aaaggttacg ttaaagaact atcaggacat ggttgtg    57

<210> SEQ ID NO 21
<211> LENGTH: 57
<212> TYPE: DNA
<213> ORGANISM: artificial
<220> FEATURE:
<223> OTHER INFORMATION: primer

<400> SEQUENCE: 21
cacaaccatg tcctgatagt tctttaacgt aaccttttca ttctcgtcaa ggtacag    57

<210> SEQ ID NO 22
<211> LENGTH: 41
<212> TYPE: DNA
<213> ORGANISM: artificial
<220> FEATURE:
<223> OTHER INFORMATION: primer

<400> SEQUENCE: 22
ccctttgtac gtggacttcg aggacgtggg gtggaatgac t    41

<210> SEQ ID NO 23
<211> LENGTH: 41

```
<212> TYPE: DNA
<213> ORGANISM: artificial
<220> FEATURE:
<223> OTHER INFORMATION: primer

<400> SEQUENCE: 23
agtcattcca ccccacgtcc tcgaagtcca cgtacaaagg g          41

<210> SEQ ID NO 24
<211> LENGTH: 34
<212> TYPE: DNA
<213> ORGANISM: artificial
<220> FEATURE:
<223> OTHER INFORMATION: primer

<400> SEQUENCE: 24
ctggattgtg gctcccaagg ggtatcacgc cttt                  34

<210> SEQ ID NO 25
<211> LENGTH: 34
<212> TYPE: DNA
<213> ORGANISM: artificial
<220> FEATURE:
<223> OTHER INFORMATION: primer

<400> SEQUENCE: 25
aaaggcgtga taccccttgg gagccacaat ccag                  34

<210> SEQ ID NO 26
<211> LENGTH: 38
<212> TYPE: DNA
<213> ORGANISM: artificial
<220> FEATURE:
<223> OTHER INFORMATION: primer

<400> SEQUENCE: 26
gctgatcatc tgaactccac taagcatgcc attgttca              38

<210> SEQ ID NO 27
<211> LENGTH: 38
<212> TYPE: DNA
<213> ORGANISM: artificial
<220> FEATURE:
<223> OTHER INFORMATION: primer

<400> SEQUENCE: 27
tgaacaatgg catgcttagt ggagttcaga tgatcagc              38

<210> SEQ ID NO 28
<211> LENGTH: 33
<212> TYPE: DNA
<213> ORGANISM: artificial
<220> FEATURE:
<223> OTHER INFORMATION: primer

<400> SEQUENCE: 28
gatcatctga actccactca tgccattgtt cag                   33

<210> SEQ ID NO 29
<211> LENGTH: 36
<212> TYPE: DNA
<213> ORGANISM: artificial
<220> FEATURE:
<223> OTHER INFORMATION: primer

<400> SEQUENCE: 29
```

-continued

```
gtctgaacaa tggcatgagt agtggagttc agatga                                    36

<210> SEQ ID NO 30
<211> LENGTH: 50
<212> TYPE: DNA
<213> ORGANISM: artificial
<220> FEATURE:
<223> OTHER INFORMATION: primer

<400> SEQUENCE: 30
gaatgaaaag gttgtattaa agtaccacta tcaggacatg gttgtggagg                     50

<210> SEQ ID NO 31
<211> LENGTH: 50
<212> TYPE: DNA
<213> ORGANISM: artificial
<220> FEATURE:
<223> OTHER INFORMATION: primer

<400> SEQUENCE: 31
cctccacaac catgtcctga tagtggtact ttaatacaac cttttcattc                     50
```

BONE MORPHOGENETIC PROTEIN 2 (BMP2) VARIANTS WITH REDUCED BMP ANTAGONIST SENSITIVITY

This is the U.S. national stage of International application PCT/EP2010/053103, filed Mar. 11, 2010 designating the United States and claiming priority to EP 09155049.1, filed Mar. 12, 2009.

The goal of this invention is to replace central residues and domains within Bone Morphogenetic Protein 2 (BMP2) which are of prime importance for the specific interactions with its inhibitors, e.g. NOGGIN. These alterations are aimed to convert this protein into an antagonist-resistant variant with increased biological activity. The new proteins are useful for BMP-related diseases or conditions.

Bone Morphogenetic Proteins (BMPs) and the related Growth & Differentiation Factors (GDFs) are phylogenetically conserved signaling proteins that belong to the Transforming Growth Factor (TGF) beta superfamily. Originally identified for their ability to induce bone, they were subsequently shown to be involved in multiple aspects of body patterning and morphogenesis (Kishigami S, Mishina Y (2005) BMP signaling and early embryonic patterning. Cytokine Growth Factor Rev 16: 265-278.). Until now there are more than 20 different BMPs known that have distinct spatiotemporal expression profiles and different functions during embryonic development and in tissue homeostasis. Despite their different functions, all BMPs share a common signaling mechanism. They are translated as precursor proteins consisting of a prodomain, which are released proteolytically after specific cleavage by members of the Subtilisin-like Proprotein Convertase family. The highly conserved mature domain is characterized by seven cysteine (Cys) residues, of which six form an intracellular Cys knot whereas the fourth of the seven Cys is important for the dimerization of BMPs. BMPs are secreted peptides that act as homo- or heterodimers and bind to two major types of membrane-spanning serine/threonine kinase receptors, the type I and type II receptors. Binding of BMPs to preformed heteromeric receptor complexes results in activation of the SMAD and other intracellular pathways.

BMP signaling is precisely regulated by a large number of antagonists, which act extracellularly, on the membrane level as well as intracellularly. A growing number of extracellular antagonists have been identified that bind to BMPs and therefore prevent receptor activation. These include Noggin (NOG), Chordin (CHRD), CHRD-like proteins (CHRDL) and the DAN family including Differential screening-selected gene Aberrant in Neuroblastoma (DAN), Cerberus 1 (CER1), COCO, Protein Related to DAN and CER (PRDC), Gremlin (GREM), Uterine Sensitization-Associated Gene 1 (USAG1), Sclerostin (SOST), Follistatin (FST), FST-like proteins (FSTL), Growth & differentiation factor-Associated Serum Protein 1 (GASP1) and Twisted Gastrulation (TWSG) (Yanagita M (2005) BMP antagonists: their roles in development and involvement in pathophysiology. Cytokine Growth Factor Rev 16: 309-317.). The inhibitors show distinct expression patterns and are thus likely to have different biological roles in vivo. In addition, antagonists have different affinities for various BMPs as well as for other factors. For example, NOG binds with high affinity to BMP2, BMP4, GDF5 and GDF6, but only with low affinity to BMP7. On the other hand, FST was originally identified as an antagonist of Activins (ACVs), but it has also been shown to bind BMPs. Various BMP antagonists might interact with similar domains in the BMP molecules, given that NOG competes with CER, GREM1 and DAN for binding to BMP2 (Canalis E, Economides A N, Gazzerro E (2003) Bone morphogenetic proteins, their antagonists, and the skeleton. Endocr Rev 24: 218-235.). It was also shown that SOST has pleiotrophic effects, by blocking BMP activity as a BMP antagonist on one hand, but also binding to and neutralizing the activity of NOG, which results in the activation of BMP activity on the other hand (Winkler D G, Yu C, Geoghegan J C, Ojala E W, Skonier J E, Shpektor D, Sutherland M K, Latham J A. 2004 Noggin and sclerostin bone morphogenetic protein antagonists form a mutually inhibitory complex. J Biol Chem 279(35):36293-8).

Thus, the large number of different BMPs is paralleled by about the same number of extracellular antagonists, but detailed knowledge of their biological importance is not available. Until now, there are at least two 3D-structures available of BMPs in complex with an antagonist (BMP7-NOG (PDB: 1M4U), and Bmp-2 with The First Von Willebrand Domain Type C Of Crossveinless-2 (PDB: 3BK3)). These structures give important information on physical interaction sites, but do not reveal which amino acids are biologically crucial for the interaction. Only few antagonists such as NOG, GREM1, FST and SOST, have been investigated for their function in skeletal development and regeneration. NOG has a central role in endochondral ossification as demonstrated by Nog null mice. These mice show a massive expansion of all cartilaginous anlagen as well as a number of other neural tube and brain defects. The importance of NOG for the development of joints was shown by the identification of mutations in NOG in patients with symphalangism and multiple synostosis (multiple joint fusions) syndrome. SOST is mutated in patients with sclerosteosis and van Buchem disease, two conditions characterised by increased bone formation (Kornak U, Mundlos S. Genetic disorders of the skeleton: a developmental approach. Am J Hum Genet. 2003 September; 73(3):447-74.).

Since their discovery it has been the intention to use the bone inductive properties of BMPs to promote osteogenesis during fracture healing or to regenerate bone after resection. However, the high potency of BMPs to induce bone in vitro and in animal models can only partly be recapitulated in human patients (Groeneveld, E. H. and E. H. Burger. 2000. Bone morphogenetic proteins in human bone regeneration. Eur J Endocrinol 142:9-21.). The BMP-effects are likely modulated by several factors such as biological availability, stability or local interacting factors in the tissue that inhibit BMPs.

The goal of the present invention is to overcome or alleviate one or more problems of the prior art. In particular it is a goal of the present invention to provide peptides with BMP2 activities which are resistant to Noggin.

According to a first aspect, the present invention provides an isolated peptide comprising or consisting of an amino acid sequence with an amino acid identity of at least 90% compared to mature human BMP2 with SEQ ID No. 1, characterized in that said amino acid sequence comprises at least two amino acid substitutions, wherein a first amino acid substitution occurs at a position corresponding to N59, S88, E94, V99, K101 and/or N102 of SEQ ID No. 1.

According to a second aspect, the present invention provides an isolated nucleic acid, characterized in that said isolated nucleic acid comprises:

i) a nucleic acid sequence encoding for an isolated peptide of the invention; or ii) a nucleic acid sequence hybridising under standard conditions to a nucleic acid encoding for an isolated peptide of the invention.

It has surprisingly been found that the isolated peptide of the invention exhibits BMP2 activity while being essentially resistant to inhibition by the natural antagonist of BMP2, Noggin. The isolated peptide of the invention is characterized by reduced susceptibility to inhibition by Noggin, is more stable in an organism, preferably in a human, than naturally occurring BMP2 and/or elicits improved or altered biological activity. Interestingly, it has been found that substitution of at least two amino acids in the C-terminal region of BMP2 leads to an isolated peptide that is essentially resistant to inhibition by Noggin while the biological BMP2 activity is basically maintained.

As used herein, the term "peptide" encompasses any molecule which comprises a linear chain of natural and/or artificial amino acids which are connected via peptide bonds. Thus, the expression "peptide" encompasses oligopeptides, polypeptides and/or protein fragments as well as whole proteins, wherein one or more of the amino acids of the peptide can be modified. As used herein, reference to specific amino acids is made based on single letter code for amino acids.

An "isolated" peptide is one that is substantially separated from other peptide molecules, which are present in the natural source of the isolated peptide (e.g., other polypeptides of the proteome of the natural source). For example, a recombinant expressed peptide is considered isolated. A peptide is also considered isolated if it has been altered by human intervention, or expressed by an organism that is not its natural source. Moreover, an "isolated" peptide can be free from some of the other cellular material with which it is naturally associated, or culture medium when produced by recombinant techniques, or chemical precursors or other chemicals when chemically synthesized. Specifically excluded from the definition of "isolated peptide" are: naturally-occurring, unpurified peptide mixtures or compositions, whole cell preparations of naturally occurring sources (including whole cell preparations that are mechanically sheared or enzymatically digested).

The present invention is also directed to isolated nucleic acids.

Nucleic acid according to the present invention may include DNA, RNA, mixtures and/or functional substituents thereof, particularly cDNA, genomic DNA and/or RNA and may be wholly or partially synthetic. The nucleic acids of the invention comprise single stranded and/or wholly or partially double stranded poly-nucleotide sequences. The term "isolated" encompasses all these possibilities. For the purpose of the present invention, where a DNA sequence is specified, e.g. with reference to a particular SEQ ID No., unless the context requires otherwise, the RNA equivalent, with U substituted for T where it occurs, is encompassed. The nucleic acid of the invention may be produced by any means, including genomic preparations, cDNA preparations, in vitro synthesis, PCR, RT-PCR, and/or in vitro or in vivo transcription.

An "isolated" nucleic acid is one that is substantially separated from other nucleic acid molecules, which are present in the natural source of the nucleic acid (e.g., sequences encoding other polypeptides). Preferably, an "isolated" nucleic acid is free of some of the sequences, which naturally flank the nucleic acid (i.e. sequences located at the 5' and 3' ends of the nucleic acid) in its naturally occurring replicon. For example, a cloned nucleic acid is considered isolated. In various embodiments, the isolated nucleic acid of the invention can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived. A nucleic acid is also considered isolated if it has been altered by human intervention, or placed in a locus or location that is not its natural site, or if it is introduced into a cell. Moreover, an "isolated" nucleic acid, such as a cDNA molecule, can be free from some of the other cellular material with which it is naturally associated, or culture medium when produced by recombinant techniques, or chemical precursors or other chemicals when chemically synthesized. Specifically excluded from the definition of "isolated nucleic acid" are: naturally-occurring chromosomes (such as chromosome spreads), genomic libraries, and whole cell genomic DNA or whole cell RNA preparations of naturally occurring sources (including whole cell preparations that are mechanically sheared or enzymatically digested). The skilled person is well aware of the degeneracy of the genetic code, allowing for a number of different nucleic acid sequences encoding for the same amino acid sequence and has no difficulties in determining whether a given nucleic acid sequence encodes for an isolated peptide of the invention.

Isolated peptides and/or nucleic acids of the present invention may be provided in isolated form, i.e. purified from their natural environment, preferably in substantially pure and/or homogeneous form and/or free or substantially free of peptides, nucleic acid and/or genes of the species of origin other than the desired sequence.

The isolated peptide of the invention comprises or consists of an amino acid sequence with an amino acid identity of at least 90% compared to mature human BMP2 with the SEQ ID No. 1, preferably the amino acid identity is at least 93%, more preferably at least 95%, even more preferably at least 98%, most preferably at least 99%. In a preferred embodiment, the isolated peptide of the invention comprises or consists of an amino acid sequence with an amino acid identity of at least 90% compared to full length human BMP2 with the SEQ ID No. 11, preferably the amino acid identity is at least 93%, more preferably at least 95%, even more preferably at least 98%, most preferably at least 99%. Said identity is calculated over the whole length of SEQ ID No. 1 or SED ID No. 11, respectively, by ignoring (excluding) the at least two amino acid substitutions present in the isolated peptide of the invention.

The full length human BMP2 protein (hBMP2) with the accession No. NP_001 191 and SEQ ID No. 11 consists of 396 amino acids. N-terminal amino acids 1 to 282, the so called prodomain with SEQ ID No. 10, are cleaved during processing of the full length peptide in order to arrive at fully processed, active hBMP2, herein also called mature hBMP2 with SEQ ID No. 1. Thus, the amino acid sequence of mature hBMP2 starts at amino acid position 283 (which is amino acid Q) of full length hBMP2 and comprises the subsequent 113 amino acids. As used herein, mature hBMP2 refers to the amino acid sequence of SEQ ID No. 1, which consists of the amino acid sequence of fully processed, active hBMP2 with a total length of 114 amino acids. Amino acid 1 of SEQ ID No. 1 refers to amino acid 283 of SEQ ID No. 11, amino acid 114 refers to amino acid 396 of SEQ ID No. 11.

In the following, particular amino acids or amino acid positions are specified by first specifying the respective amino acid of hBMP2 in one letter code followed by the position number within the amino acid sequence of SEQ ID No. 1 read starting at the N-terminus into C-terminal direction. For example, the first amino acid at the N-terminus of SEQ ID No. 1 is described as Q1 (identical to Q283 of SEQ ID No. 11), whereas the C-terminal end of SEQ ID No. 1 is expressed as R114 (corresponding to R396 of SEQ ID No. 11). For historical reasons in the experimental section of this application, particular amino acid positions are specified by the position number within the amino acid sequence of full length human BMP2 with SEQ ID No. 11 read starting at the N-terminus into C-terminal direction. A particular amino acid or amino acid position defined relative to full length BMP2 (SEQ ID No. 11) can easily be transferred into a definition with respect to mature BMP2 (SEQ ID No. 1) simply by subtracting 282 from the position number. E.g. amino acid N341 of SEQ ID No. 11 is identical to N59 of SEQ ID No. 1.

Identity or homology between two amino acid sequences is understood as meaning the identity of the respective sequences over the whole sequence length in each case (the terms identity and homology are used interchangeably here within). To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). The percent identity between the two sequences is a function of the number of identical positions shared by the sequences (i.e., % homology=# of identical positions/total # of positions×100). The determination of percent homology between two sequences can be accomplished using a mathematical algorithm. A preferred, non-limiting example of a mathematical algorithm utilized for the comparison of two sequences is the algorithm of Karlin and Altschul (1990) Proc. Natl. Acad. ScL USA 87:2264-68, modified as in Karlin and Altschul (1993) Proc. Natl. Acad. ScL USA 90:5873-77. Such an algorithm is incorporated into the NBLAST and XBLAST programs of Altschul, et al. (1990) J. Mol. Biol. 215:403-10. BLAST nucleotide searches can be performed with the NBLAST program, score=100, wordlength=12. BLAST protein searches can be performed with the XBLAST program, score=50, wordlength=3. To obtain gapped alignments for comparison purposes, Gapped BLAST can be utilized as described in Altschul et al, (1997) Nucleic Acids Research 25(17):3389-3402. When utilizing BLAST and Gapped BLAST programs, the default parameters of the respective programs (e.g., XBLAST and NBLAST) can be used. Alternatively identity or homology can be determined by comparison with the aid of the ClustalW_Bioedit algorithm (Thompson J D et al. (1994) Nucleic Acids Res 22:4673-4680) using default settings in software package Bioedit.

Preferably, the isolated peptide of the invention exhibits BMP2 activity. The isolated peptide of the invention is classified as exhibiting BMP2 activity if the isolated peptide retains at least 25% of wild type BMP2 activity, i.e. activity of processed, active human BMP2 with SEQ ID No. 1. Preferably the isolated peptide of the invention exhibits at least 50% of wild type BMP2 activity, more preferably at least 75%, even more preferably at least 85% and most preferably at least 95%. BMP2 activity can be measured in a number of different ways. As long as BMP2 activity of the isolated peptide of the invention and the control (active human BMP2) are determined in one and the same test, the exact nature of the BMP2 activity test is less important. The skilled person is well aware of a number of different tests that are suitable to test BMP2 activity. Preferably BMP2 activity is tested using the chicken micromass culture system (chMM) test. The chicken micromass culture system (chMM) is an in vitro model for cartilage differentiation (DeLise A M, Stringa E, Woodward W A, Mello M A, Tuan R S 2000 Embryonic limb mesenchyme micromass culture as an in vitro model for chondrogenesis and cartilage maturation. Methods Mol Biol. 137:359-75.) (Seemann P, Schwappacher R, Kjaer K W, Krakow D, Lehmann K, Dawson K, Stricker S, Pohl J, Ploger F, Staub E, Nickel J, Sebald W, Knaus P, Mundlos S. 2005 Activating and deactivating mutations in the receptor interaction site of GDF5 cause symphalangism or brachydactyly type A2. J Clin Invest. 2005 September; 115(9):2373-81.). Here, primary mesenchymal cells prepared from chicken limb buds differentiate into chondrocytes. Extracellular matrix production is used as a marker for early chondrogenesis and can be quantified using Alcian blue staining after incubation for three to seven days. To test a specific gene in this system, the cells are infected with a replication competent avian sarcoma (RCAS) virus with the gene of interest incorporated. Overexpression of hBMP2 in the chMM is known to induce cell proliferation and chondrogenic matrix production dramatically (Duprez D M, Coltey M, Amthor H, Brickell P M, Tickle C. 1996 Bone morphogenetic protein-2 (BMP-2) inhibits muscle development and promotes cartilage formation in chick limb bud cultures. Dev Biol. March 15; 174(2):448-52.). In contrast, co-expression of Noggin and hBMP2 leads to a complete inhibition of the described differentiation effects.

In addition to the sequence identity compared to SEQ ID No. 1 and/or SEQ ID No. 11, the isolated peptide of the invention is further characterized in that said amino acid sequence comprises at least two amino acid substitutions, wherein a first amino acid substitution occurs at a position corresponding to N59, S88, E94, V99, K101 and/or N102 of SEQ ID No. 1. As used herein, the term amino acid substitution refers to the deletion and/or replacement of a specific amino acid of a given position. In a particular preferred way, the term amino acid substitution can be understood to refer solely to replacement of a specific amino acid of a given position. In order to be specific each substitution is described at least by the type of amino acid to be substituted, preferably in one letter code, and by giving the exact position of said amino acid based on SEQ ID No. 1. A particular substitution can further be specified by naming the amino acid(s) used to replace the amino acid to be substituted. In any case, with a particular substitution only the specified amino acid named before the position number is substituted. A substitution may result in deletion of said amino acid from the sequence, in replacement of said amino acid by exactly one other amino acid and/or in replacement of said amino acid by more than one other amino acid, preferably by not more than three other amino acids, more preferably by two other amino acids.

Preferably the isolated peptide of the invention is characterized in that the first amino acid substitution is selected from N59K, N59T, N59V, N59E, S88A, E94P, V99T, V99Y, K101I, K101L, N102S, N102V, N102W and/or N102YH. More preferably the isolated peptide of the invention comprises at least one substitution at position N59, E94, K101 and/or N102, most preferably at position N59 or N102. In a further more preferred embodiment, the isolated peptide of the invention is characterized in that the first amino acid substitution is selected from N59K, N59T, N59V, N59E, E94P, K101I, K101L, N102S, N102V, N102W and/or N102YH.

In a further preferred embodiment, the isolated peptide of the invention is characterized in that the isolated peptide comprises a second amino acid substitution, wherein the second amino acid substitution is different from the first amino acid substitution and occurs at a position corresponding to D22, S24, V26, N29, D30, V33, A34, P36, G37, H39, F41, H44, P48, A52, D53, L55, N59, S88, E94, V99, K101 and/or N102 of SEQ ID No. 1. More preferably the isolated peptide of the invention is characterized in that the second amino acid substitution is selected from D22R, D22S, D22H, S24G, S24H, S24E, S24Q, V26L, N29T, N29Q, D30A, D30T, V33I, V33R, A34Y, A34D, P36K, P36R, P36S, G37T, H39A, F41N, H44D, P48D, A52N, D53A, D53Y, L55M, N59K, N59T, N59V, N59E, S88A, E94P, V99T, V99Y, K101I, K101L, N102S, N102V, N102W and/or N102YH.

In another preferred embodiment, the isolated peptide of the invention is characterized in that the second amino acid substitution occurs at a position corresponding to D22, S24, N29, D30, V33, A34, P36, G37, D53, N59, S88, E94, V99, K101 and/or N102 of SEQ ID No. 1. More preferably the isolated peptide of the invention is characterized in that the second amino acid substitution is selected from D22R, D22S, D22H, S24G, S24H, S24E, N29T, D30A, D30T, V33R, A34Y, A34D, P36K, P36R, P36S, G37T, D53Y, N59K, N59T, N59V, N59E, S88A, E94P, V99T, V99Y, K101I, K101L, N102S, N102V, N102W and/or N102YH.

In a further preferred embodiment, the isolated peptide of the invention is characterized in that the isolated peptide comprises a third amino acid substitution, wherein the third amino acid substitution is different from the first and second amino acid substitution and occurs at a position corresponding to D22, S24, N29, D30, V33, A34, P36, G37, D53, N59, S88, E94, V99, K101 and/or N102 of SEQ ID No. 1. More preferably the isolated peptide of the invention is characterized in that the third amino acid substitution is selected from D22R, D22H, S24G, S24H, S24E, N29T, D30A, D30T, V33R, A34Y, A34D, P36K, P36R, P36S, G37T, D53Y, N59K, N59T, N59V, N59E, S88A, E94P, V99T, V99Y, K101I, K101L, N102V, N102YH, N102S and/or N102W.

In a further preferred embodiment, the isolated peptide of the invention is characterized in that the isolated peptide comprises a forth amino acid substitution, wherein the forth amino acid substitution is different from the first, second and third amino acid substitution and occurs at a position corresponding to D22, S24, N29, D30, V33, A34, P36, G37, D53, N59, S88, E94, V99, K101 and/or N102 of SEQ ID No. 1. More preferably the isolated peptide of the invention is characterized in that the forth amino acid substitution is selected from D22R, D22H, S24G, S24H, S24E, N29T, D30A, D30T, V33R, A34Y, A34D, P36K, P36R, P36S, G37T, D53Y, N59K, N59T, N59V, N59E, S88A, E94P, V99T, V99Y, K101I, K101L, N102V, N102YH, N102S and/or N102W.

The isolated peptide of the invention can comprise or consist of an amino acid sequence with:
SEQ ID No. 2, which is based on SEQ ID No. 1 and substitutions N59K and V99T;
SEQ ID No. 3, which is based on SEQ ID No. 1 and substitutions N59K and N102YH;
SEQ ID No. 4, which is based on SEQ ID No. 1 and substitutions N59T and V99T;
SEQ ID No. 5, which is based on SEQ ID No. 1 and substitutions N59T and N102YH;
SEQ ID No. 6, which is based on SEQ ID No. 1 and substitutions V99T and N102YH.
SEQ ID No. 7, which is based on SEQ ID No. 1 and substitutions N59T and S24E;
SEQ ID No. 8, which is based on SEQ ID No. 1 and substitutions N59K and P36K;
SEQ ID No. 9, which is based on SEQ ID No. 1 and substitutions N59K, N102YH and S24E;
SEQ ID No. 12, which is based on SEQ ID No. 11 and substitutions N59K and V99T;
SEQ ID No. 13, which is based on SEQ ID No. 11 and substitutions N59K and N102YH;
SEQ ID No. 14, which is based on SEQ ID No. 11 and substitutions N59T and V99T;
SEQ ID No. 15, which is based on SEQ ID No. 11 and substitutions N59T and N102YH;
SEQ ID No. 16, which is based on SEQ ID No. 11 and substitutions V99T and N102YH.
SEQ ID No. 17, which is based on SEQ ID No. 11 and substitutions N59T and S24E;
SEQ ID No. 18, which is based on SEQ ID No. 11 and substitutions N59K and P36K; and/or
SEQ ID No. 19, which is based on SEQ ID No. 11 and substitutions N59K, N102YH and S24E;

The isolated peptide of the invention may comprise further amino acid substitutions that are present in addition to the at least two amino acid substitutions defined above.

The isolated peptide of the invention may contain further modifications, for instance mutations that alter additional protein properties. Such properties may include BMP2 activity, resistance to Noggin and/or other inhibitors or antagonists of BMP2 as well as properties such as stability or immunogenicity or which enable or prevent posttranslational modifications such as PEGylation or glycosylation. Isolated peptides of the invention may be subjected to co- or post-translational modifications, including but not limited to synthetic derivatization of one or more side chains or termini, glycosylation, PEGylation, circular permutation, cyclization, fusion to proteins or protein domains, and addition of peptide tags or labels.

The isolated peptide of the invention can be prepared according to known methods. Such methods encompass the synthetic de novo synthesis of such isolated peptides and/or the expression of isolated peptides of the invention from a nucleic acid encoding for an isolated peptide. In a particular preferred way, the isolated peptide of the invention is prepared by expression using an isolated nucleic acid of the invention.

The present invention also refers to an isolated nucleic acid comprising or consisting of a nucleic acid sequence encoding for an isolated peptide of the invention or comprising or consisting of a nucleic acid sequence hybridising under standard conditions to a nucleic acid sequence encoding for an isolated peptide of the invention. The term standard hybridization condition is to be understood broadly and means both stringent and/or less stringent hybridization conditions. Such hybridization conditions are described inter alia in Sambrook J, Fritsch E F, Maniatis T et al., in Molecular Cloning—A Laboratory Manual, 2nd edition, Cold Spring Harbor Laboratory Press, 1989, pages 9.31-9.57 or in Current Protocols in Molecular Biology, John Wiley & Sons, N.Y. (1989), 6.3.1-6.3.6. For example, the conditions during the washing step(s) can be selected from the range of conditions limited by those of low stringency (with approximately 2*SSC at 50° C.) and of high stringency (with approximately 0.2*SSC at 50° C., preferably at 65° C.) (20*SSC: 0.3 M sodium citrate, 3 M NaCl, pH 7.0). In addition, the temperature during the washing step can be raised from low-stringency conditions at room temperature, approximately 22° C., to more stringent conditions at approximately 65° C. Both parameters, the salt concentration and the temperature, can be varied simultaneously, and it is also possible for one of the two parameters to be kept constant and only the other to be varied. It is also possible to employ denaturing agents such as, for example, form amide or SDS during the hybridization. Hybridization in the presence of 50% formamide is preferably carried out at 42° C. Some exemplary conditions for hybridization and washing steps are given below:

(1) Hybridization conditions with for example
a) 4*SSC at 65° C., or
b) 6*SSC, 0.5% SDS, 100 µg/ml denatured fragmented salmon sperm DNA at 65° C., or
c) 4*SSC, 50% formamide, at 42° C., or
d) 2* or 4*SSC at 50° C. (low-stringency condition), or
e) 2* or 4*SSC, 30 to 40% formamide at 42° C. (low-stringency condition), or
f) 6*SSC at 45° C., or,
g) 0.05 M sodium phosphate buffer pH 7.0, 2 mM EDTA, 1% BSA and 7% SDS.

(2) Washing steps with for example
a) 0.1*SSC at 65° C., or
b) 0.1*SSC, 0.5% SDS at 68° C., or
c) 0.1*SSC, 0.5% SDS, 50% formamide at 42° C., or
d) 0.2*SSC, 0.1% SDS at 42° C., or
e) 2*SSC at 65° C. (low-stringency condition), or
f) 40 mM sodium phosphate buffer pH 7.0, 1% SDS, 2 mM EDTA.

Isolated nucleic acids of the invention can be prepared according to methods known in the art. In a preferred way, isolated nucleic acids of the invention can be prepared by total gene synthesis, or by site-directed mutagenesis of a nucleic acid encoding wild type or modified BMPs. Methods including template-directed ligation, recursive PCR, cassette mutagenesis, site-directed mutagenesis or other techniques that are well known in the art may be utilized (see for example Strizhov et al. PNAS 93:15012-15017 (1996), Prodromou and Peri, Prot. Eng. 5: 827-829 (1992), Jayaraman and Puccini, Biotechniques 12: 392-398 (1992), and Chalmers et al. Biotechniques 30: 249-252 (2001)).

The isolated nucleic acid of the present invention may comprise further nucleic acid sequences which may add further functions to the isolated nucleic acid of the invention. For example such additional nucleic acid sequences may comprise nucleic acid sequences that allow for proper expression of an isolated peptide of the invention and may encompass promoter sequences, regulatory sequences, stop signals, replication origins and the like. The skilled person is well aware of such functional nucleic acid sequences and of how to arrange them in order to arrive at a nucleic acid molecule with the desired properties.

The present invention refers also to a transgenic organism or cell expressing an isolated peptide of the invention. Preferably said transgenic organism or cell is characterized in that said organism or cell comprises a isolated nucleic acid of the invention. Thus, the present invention relates to transgenic organisms or cells transiently or stably transformed or transfected with at least one isolated nucleic acid or at least one transgenic expression cassette or at least one vector encoding for an isolated peptide of the invention or to progeny of such transgenic organisms or cells. Furthermore the present invention relates to cells, cell cultures, tissues and/or parts of transgenic organisms of the invention. It is understood that for the purpose of the present invention the term transgenic organism not only encompasses the organism where the nucleic acid of the invention has been transiently or stably introduced, but also refers to the progeny of such organisms irrespective of the generation distance, e.g. progeny of first generation as well as progeny of the $X^{th}$ generation, provided that these organisms still comprise the nucleic acid of the invention and/or express the isolated peptide of the invention.

Preferably the transgenic organism or cell is of prokaryotic or eukaryotic origin, preferably the transgenic organism is a microorganism. Preferred microorganisms are bacteria, yeasts, algae or fungi.

The preparation of a transformed organism or of a transformed cell requires introducing the appropriate DNA into the appropriate host organism or cell. A multiplicity of methods is available for this process which is referred to as transformation (see also Keown et al. 1990 Methods in Enzymology 185:527-537). Thus, by way of example, the DNA may be introduced directly by microinjection or by bombardment with DNA-coated microparticles or nanoparticles. The cell may also be permeabilized chemically, for example using polyethylene glycol, so that the DNA can enter the cell via diffusion. The DNA may also be performed via protoplast fusion with other DNA-containing units such as minicells, cells, lysosomes or liposomes. Another suitable method for introducing DNA is electroporation in which the cells are reversibly permeabilized by an electric impulse.

The present invention is also directed to the isolated peptide of the invention and/or the isolated nucleic acid of the invention for use in the treatment of a disease or condition, e.g. for treatment of BMP-related diseases or conditions, wherein such diseases or conditions comprise:
  formation of bone, cartilage, non-mineralized skeletal or connective tissue;
  metabolic disease, for example treatment of loss and/or increase of bone mass in metabolic bone diseases (U.S. Pat. No. 5,674,844);
  replacement or repair of bone and/or cartilage at injury sites such as breaks, fractures and/or tears (U.S. Pat. No. 5,733,878), e.g. repair of the spine or vertebrae;
  periodontal tissue regeneration (U.S. Pat. No. 5,733,878);
  liver regeneration (U.S. Pat. No. 5,849,686);
  chronic renal failure (U.S. Pat. No. 6,861,404);
  enhancement of functional recovery following central nervous system ischemia or trauma (U.S. Pat. No. 6,407,060);
  dendritic growth (U.S. Pat. No. 6,949,505);
  neural cell adhesion (U.S. Pat. No. 6,800,603);
  Parkinson's disease (U.S. Pat. No. 6,506,729).

As used herein, the term "treating" refers to reversing, alleviating or inhibiting the progress of a disease, disorder or condition, or one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein "treating" may also refer to preventing the recurrence of a disease, disorder or condition or of one or more symptoms associated with such disease, disorder or condition. The terms "treatment" and "therapeutically," as used herein, refer to the act of treating, as "treating" is defined above.

The peptide and/or an isolated nucleic acid of the invention may be used in the manufacture of a medicament, preferably in the manufacture of a medicament for treatment of BMP-related diseases or conditions, wherein such diseases or conditions comprise formation of bone, cartilage, non-mineralized skeletal or connective tissue, metabolic disease, replacement or repair of bone and/or cartilage at injury sites such as breaks, fractures and/or tears, periodontal tissue regeneration, liver regeneration, chronic renal failure, enhancement of functional recovery following central nervous system ischemia or trauma, dendritic growth, neural cell adhesion, Parkinson's disease.

The present invention is also directed to a pharmaceutical composition comprising a peptide and/or an isolated nucleic acid of the invention and optionally one or more pharmaceutically acceptable excipients. When used in human therapy, the isolated peptide or nucleic acid of the invention and/or their pharmaceutically acceptable salts will generally be administered as a formulation in association with one or more pharmaceutically acceptable excipients. The term "excipient" is used herein to describe any ingredient other than the compound of the invention. The choice of excipient will to a large extent depend on the particular mode of administration.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include: solid formulations such as tablets; capsules containing particulates, liquids, or powders; lozenges (including liquid-filled); and chews; multi- and nano-particulates; gels; solid solutions; liposomes; films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in the state of the art.

For tablet dosage forms, depending on dose, the drug may make up from 1 weight to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatine, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also may contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is standard in the art.

Consumable oral films for human use are typically pliable water-soluble or water-swellable thin film dosage forms which may be rapidly dissolving or mucoadhesive and typically comprise isolated peptide or nucleic acid, a film-forming polymer, a binder, a solvent, a humectant, a plasticiser, a stabiliser or emulsifier, a viscosity-modifying agent and a solvent. Some components of the formulation may perform more than one function.

The isolated peptide or nucleic acid of the invention may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the isolated peptide or nucleic acid of the invention may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in the art. The use of chewing gum to achieve controlled release is described e.g. in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of isolated peptide or nucleic acid of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLApoly(dl-lactic-coglycolic) acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerine, polyethylene glycol and propylene glycol. Penetration enhancers may be incorporated.

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of isolated peptide or nucleic acid of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Formulations for inhaled/intranasal administration may be formulated to be immediate and/or modified release using, for example, PGLA, Modified release formulations include delayed-, sustained-, pulsed-, controlled-, targeted and programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes, both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 0.001 mg to 5000 mg depending, of course, on the mode of administration. For example, an intravenous daily dose may only require from 0.001 mg to 40 mg, the total daily dose may be administered in single or divided doses and may, at the physician's discretion, fall outside of the typical range given herein. These dosages are based on an average human subject having a weight of about 65 kg to 70 kg. The physician will readily be able to determine doses for subjects whose weight falls outside this range, such as infants and the elderly.

In a further aspect, the present invention provides a method of treatment of of BMP-related diseases or conditions, wherein such diseases or conditions comprise formation of bone, cartilage, non-mineralized skeletal or connective tissue, metabolic disease, replacement or repair of bone and/or cartilage at injury sites such as breaks, fractures and/or tears, periodontal tissue regeneration, liver regeneration, chronic renal failure, enhancement of functional recovery following central nervous system ischemia or trauma, dendritic growth, neural cell adhesion, Parkinson's disease, characterized in that a subject in need of such treatment is administered an effective dose of an isolated peptide of the invention and/or an isolated nucleic acid of the invention, optionally together with one or more pharmaceutically acceptable excipients.

According to the present invention, the isolated peptide, isolated nucleic acid and/or a medicament comprising the same as active ingredient is administered preferably at an effective dose. An "effective dose" is the dose of an active ingredient that upon administration to a patient yields a measurable therapeutical effect with regard to the disease of interest. In the present invention an effective dose is the dose of the isolated peptide or nucleic acid that upon administration to a patient yields a therapeutic effect with regard to one or more of the diseases or conditions specified above in patients suffering there from. Preferably the isolated peptide or nucleic acid is administered at a dose of not more than 5 mg/kg body weight per treatment or administration. In particular the isolated peptide or nucleic acid of the invention can be administered at a dose of 1 ng/kg to 1 g/kg body weight per treatment or administration, preferably of 0.01 µg/kg to 5000 µg/kg body weight per treatment or administration. In order to prevent acute side effects to occur, it is recommended that the isolated peptide or nucleic acid is administered at a maximum cumulative daily dose of not more than 10 mg/kg body weight.

In the following experimental section, the invention will be explained in further detail by way of figures and examples.

Throughout the experimental section and the figures, particular amino acids and amino acid positions are referred to in respect to SEQ ID No. 11. These amino acids and amino acid positions can easily be translated into amino acids and amino acid positions in respect to SEQ ID No. 1 simply by subtracting 282 from the position number.

FIGURES

Figure 2:
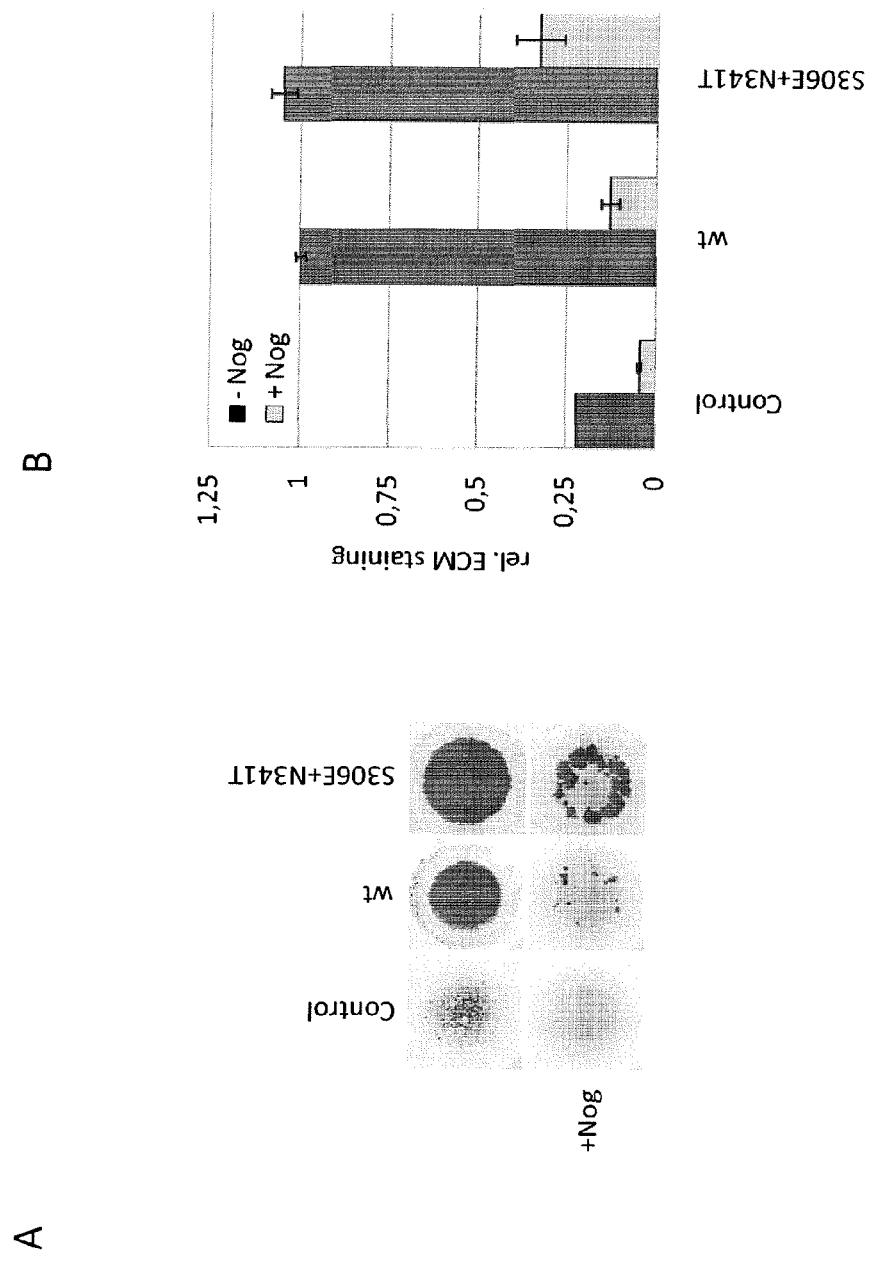
Figure 3:
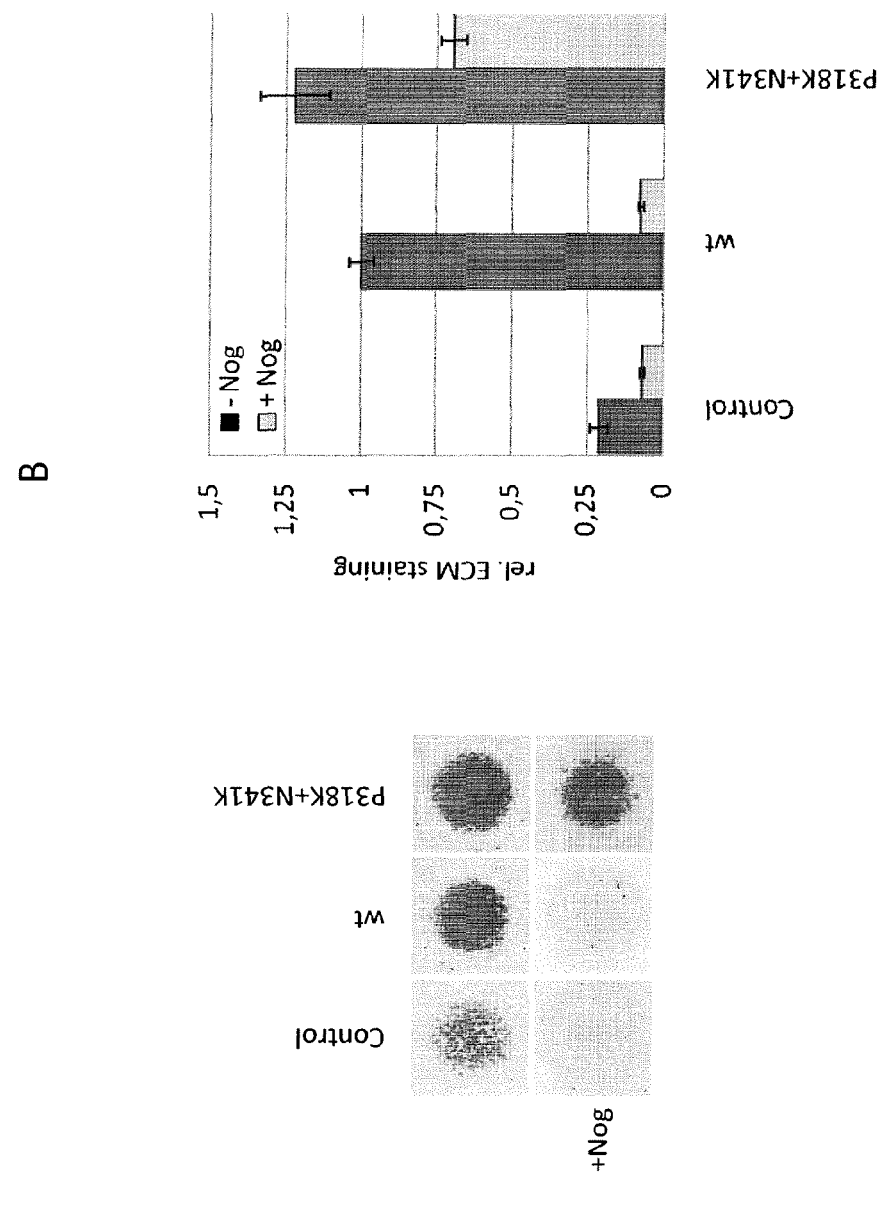
Figure 4:
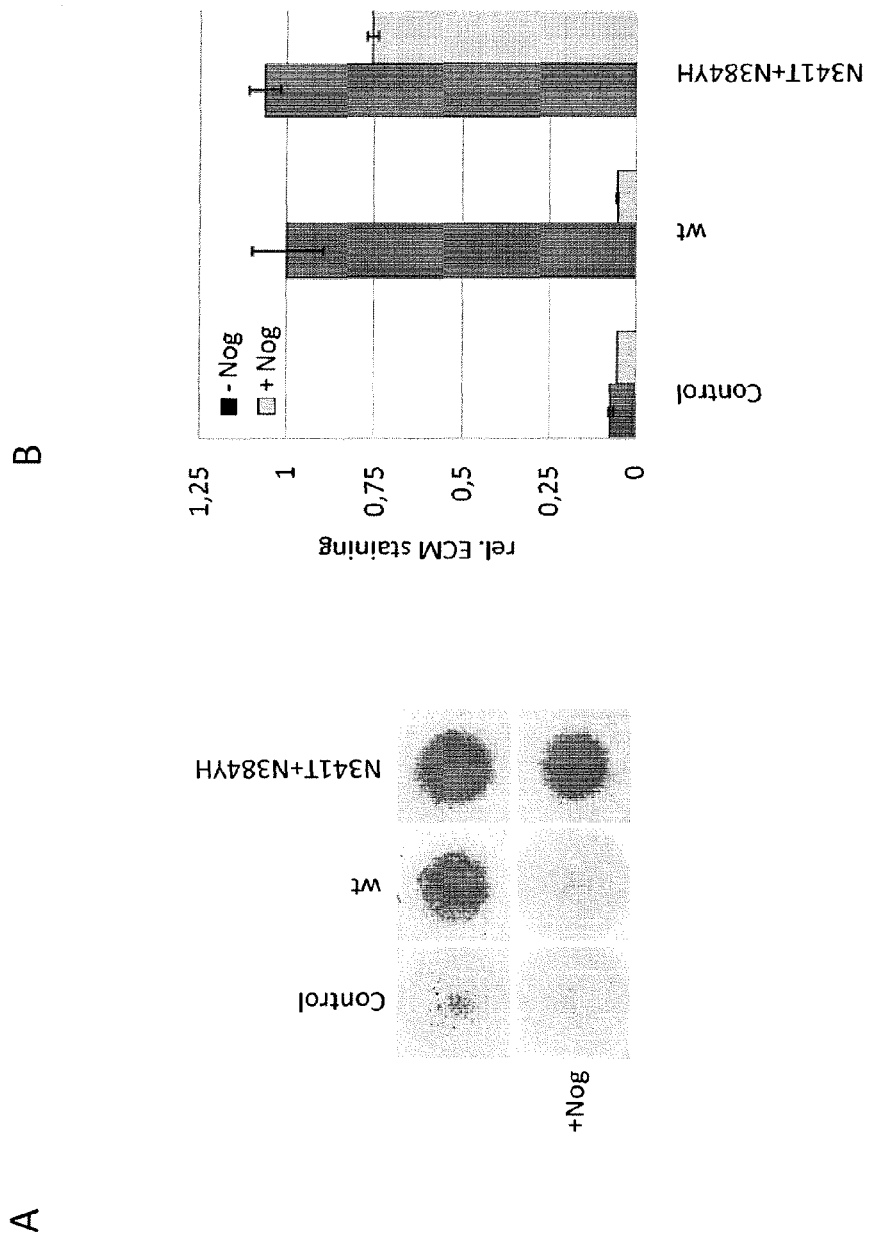
Figure 5:
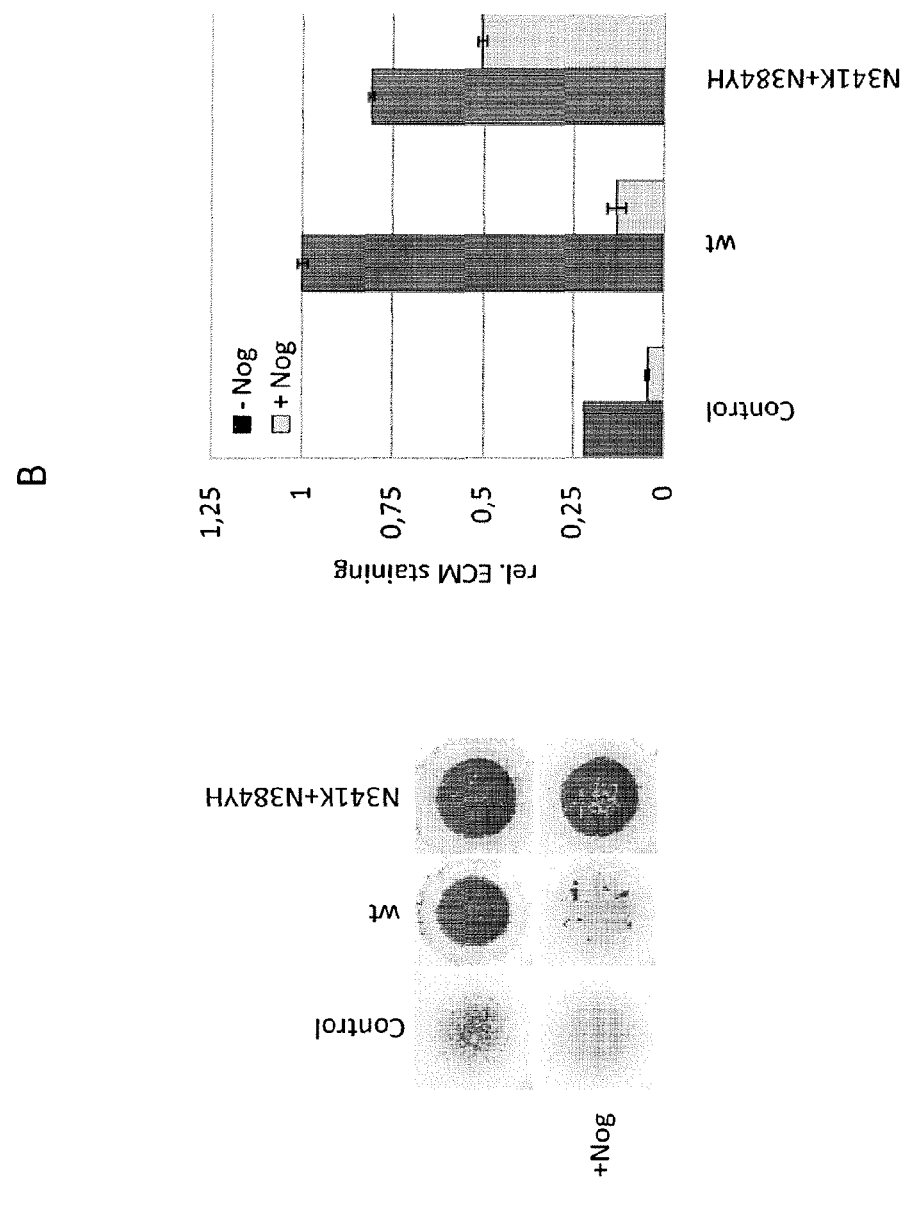
Figure 6:
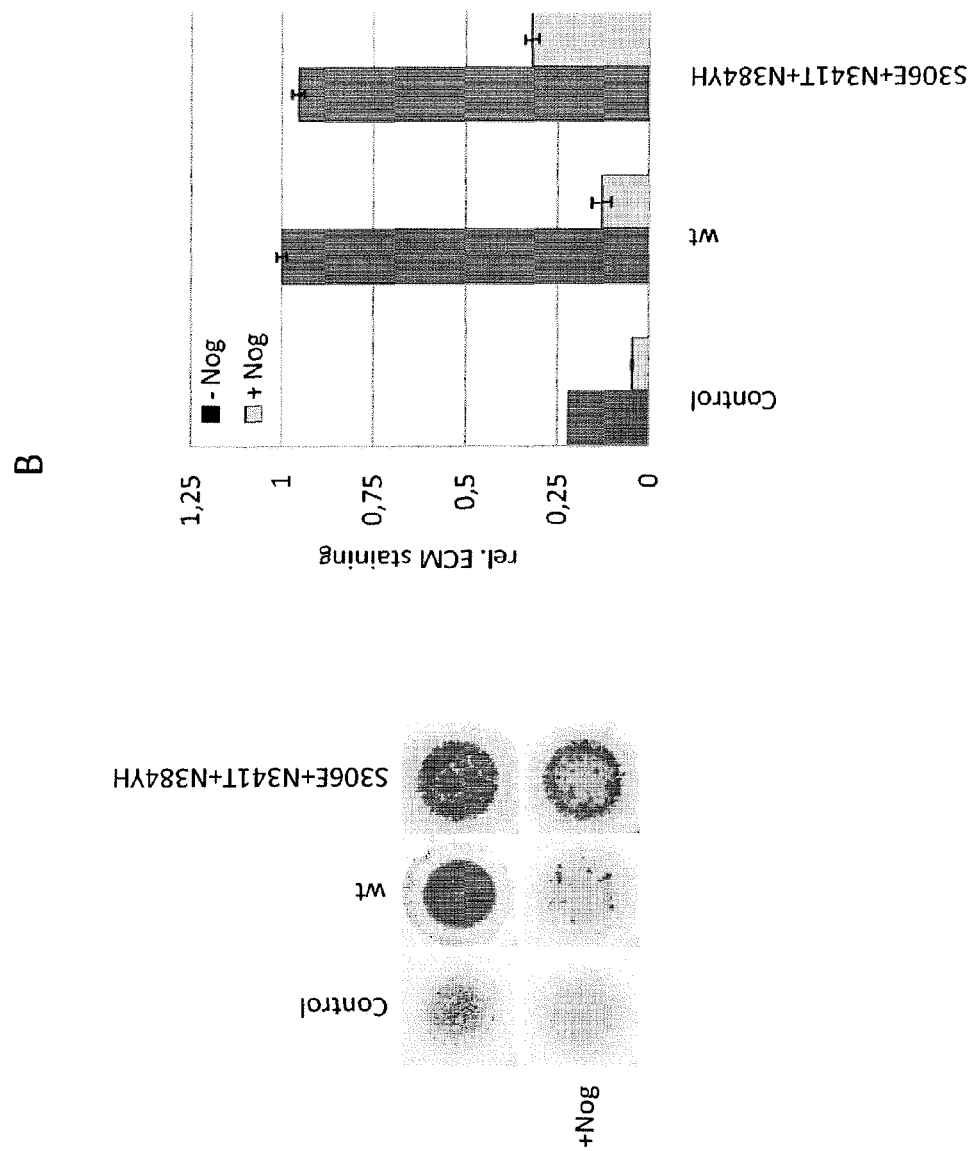
Figure 7:
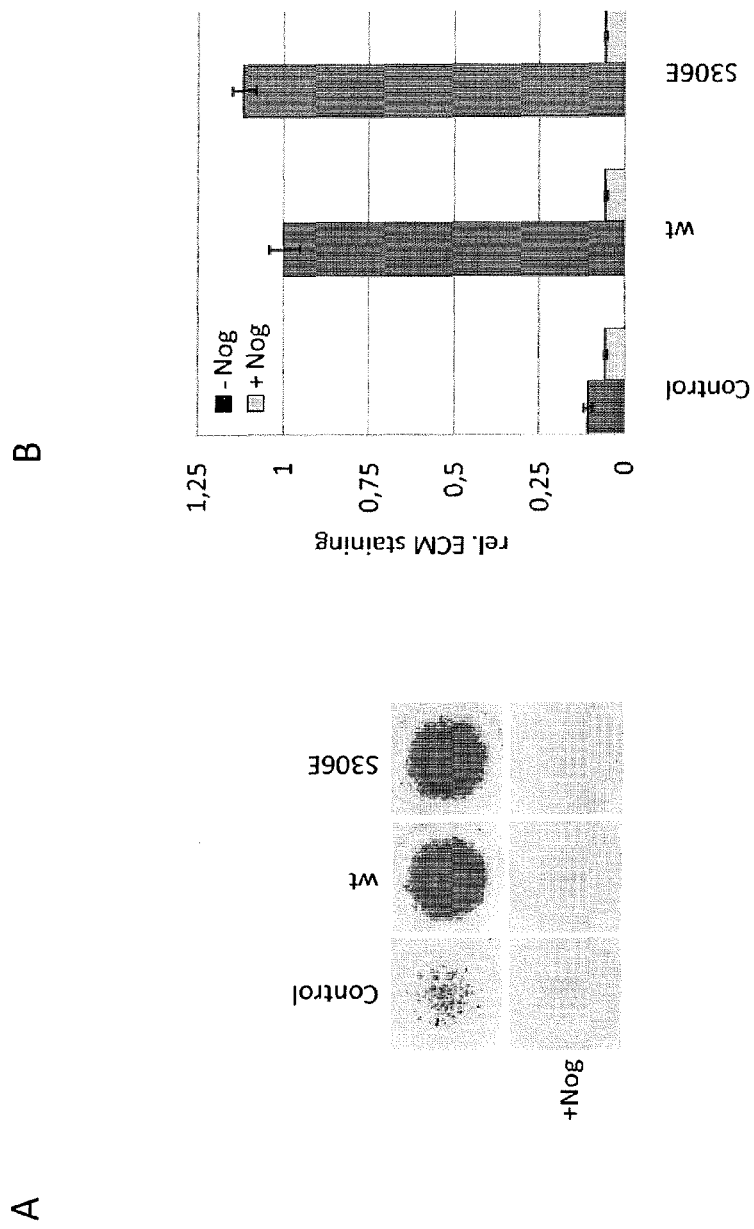
Figure 8:
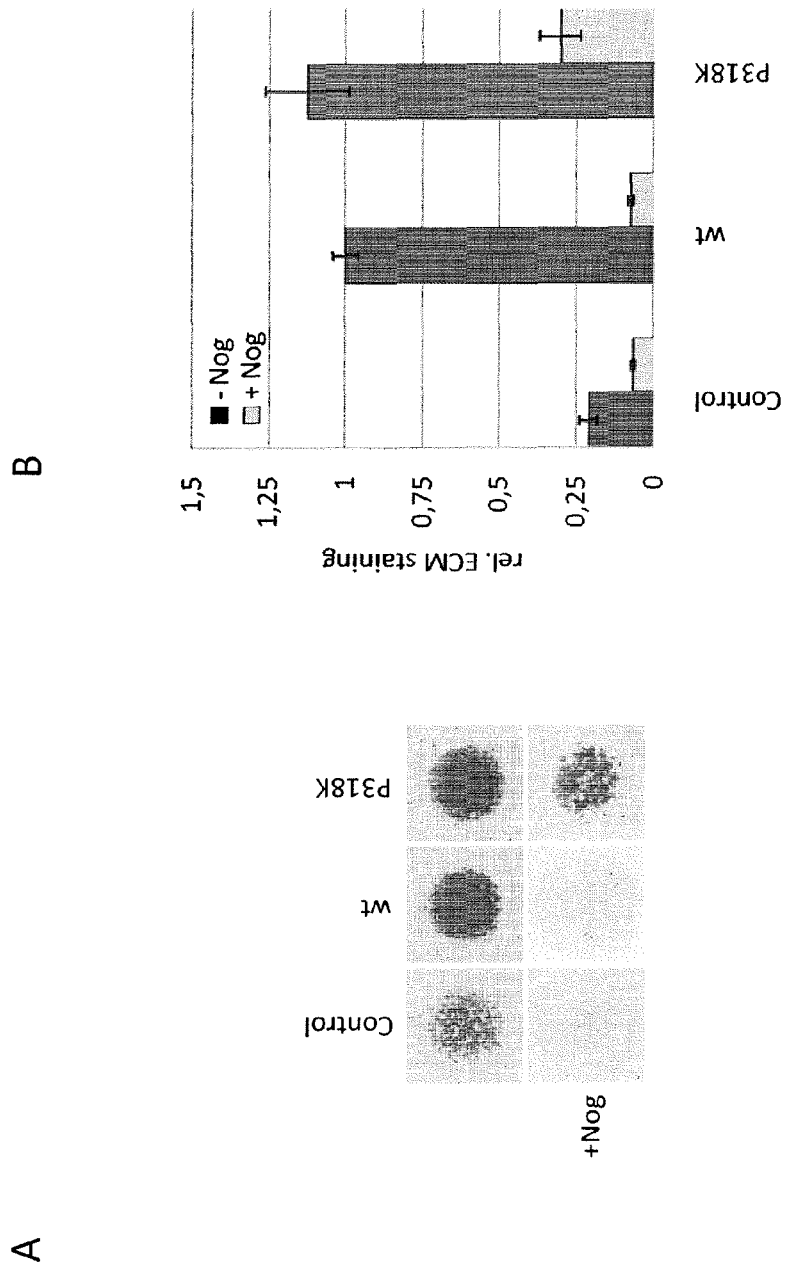
Figure 9:
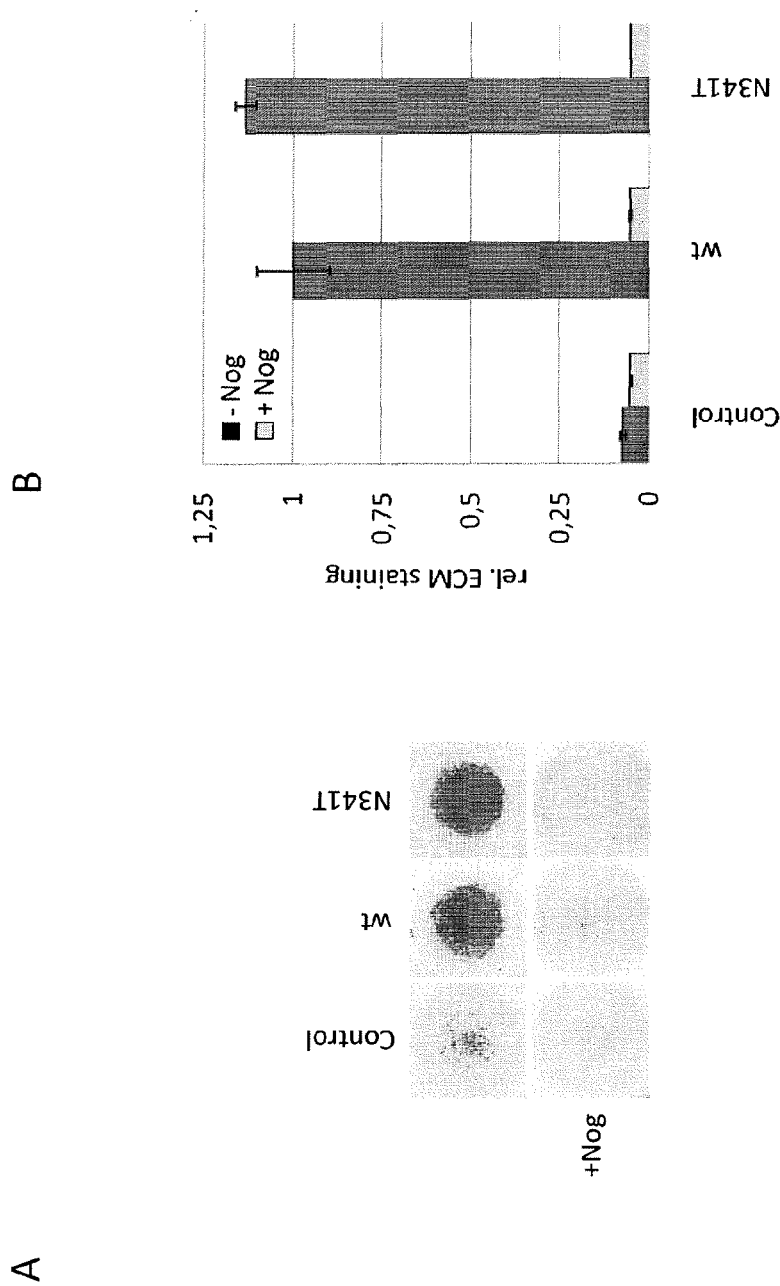
Figure 10:
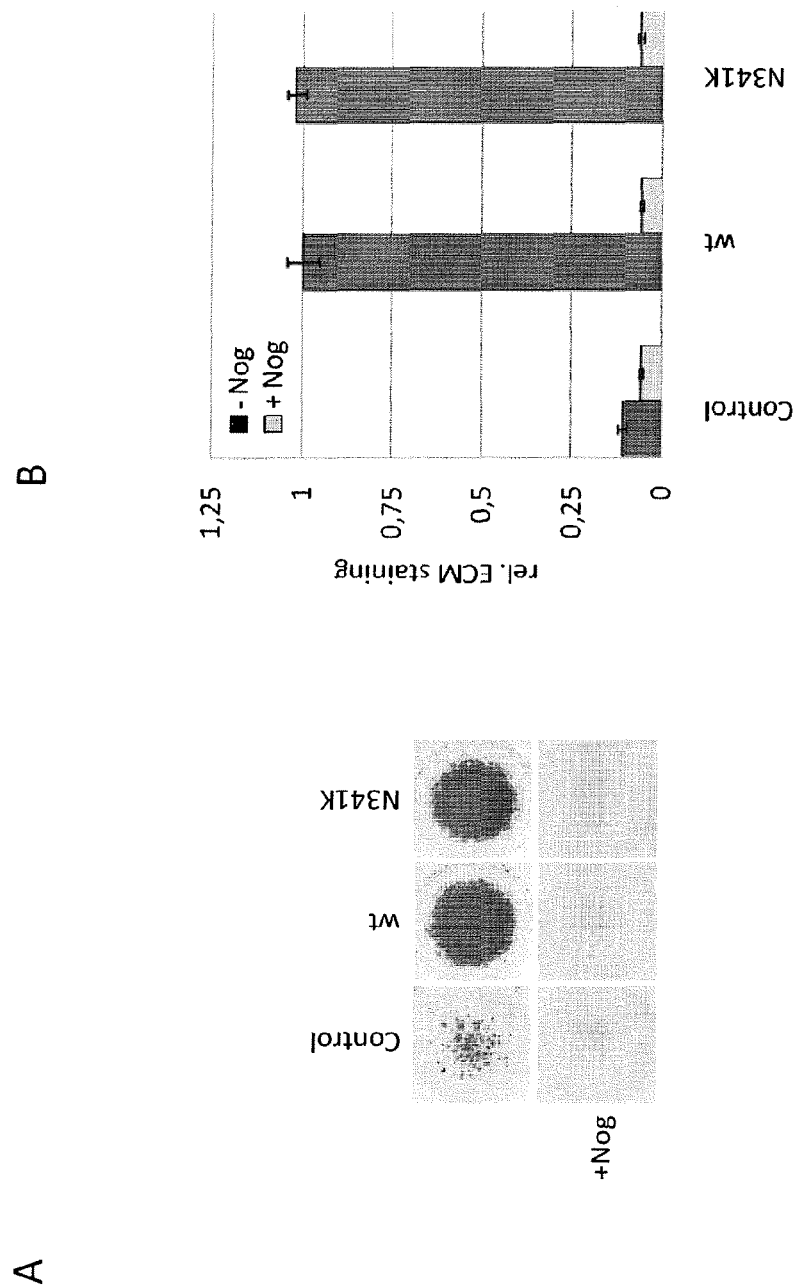
Figure 11:
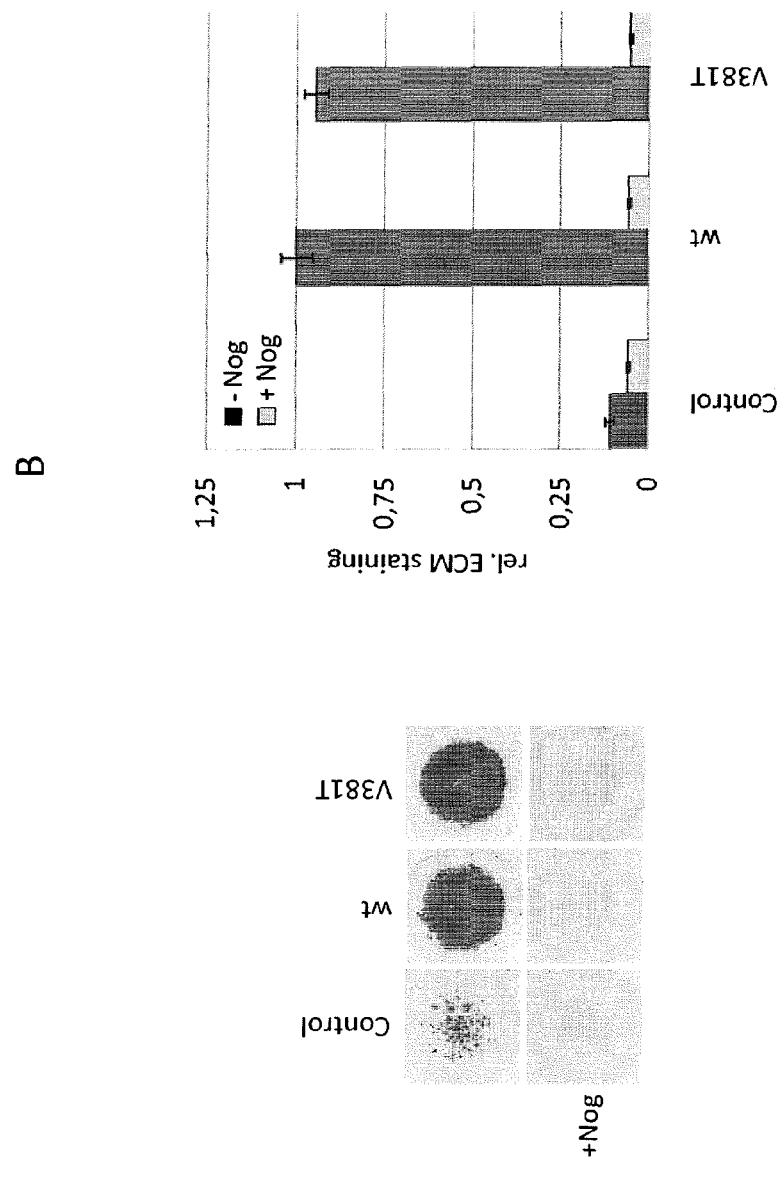
Figure 12:
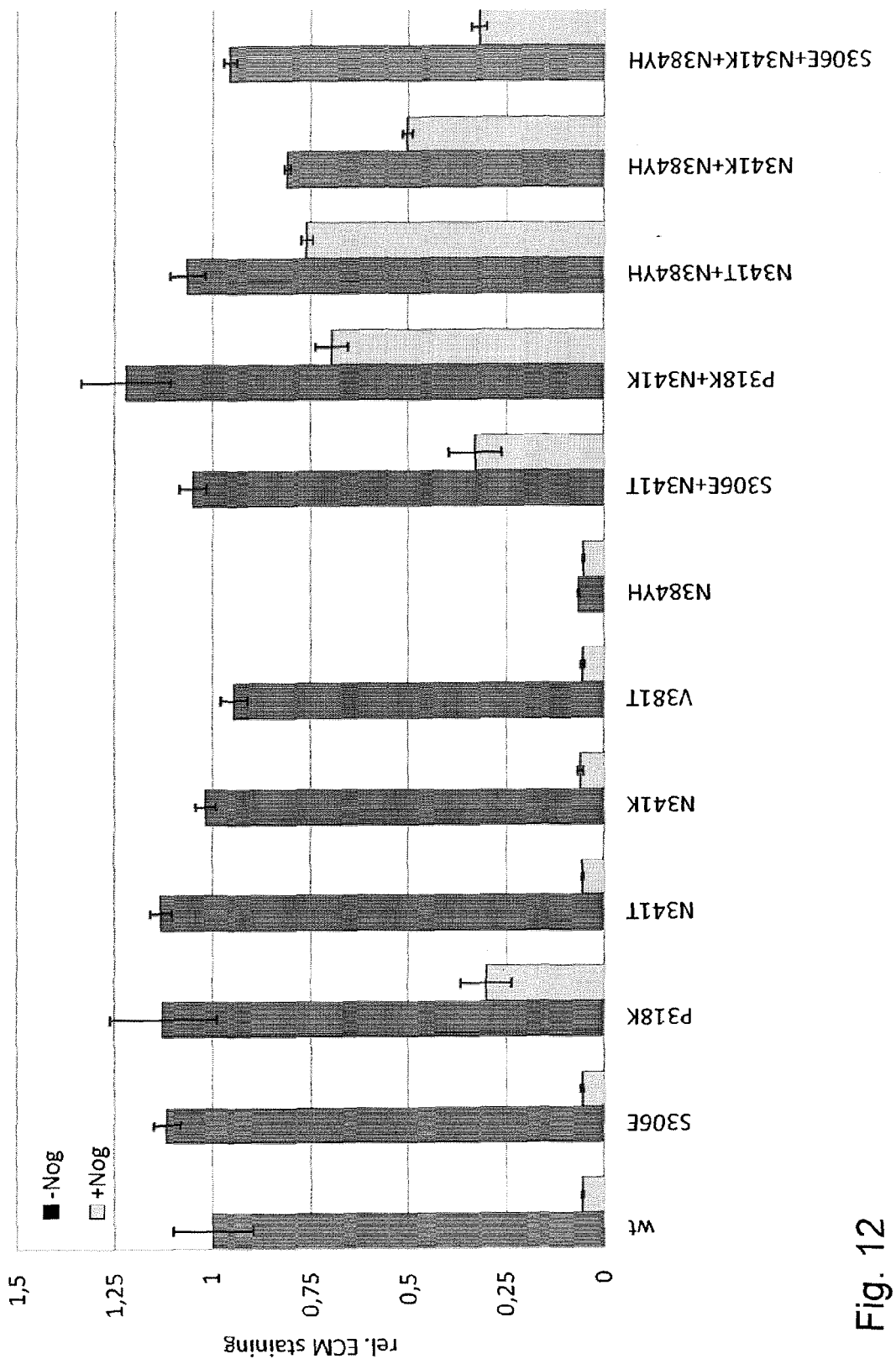

FIG. 1 shows the effect of BMP2 with N384YH substitution on chondrogenesis with or without presence of Noggin in chMM test; (A) shows Alcian blue stained cartilaginous extracellular matrix of mesenchymal precursor cells in the chick micromass; (B) shows quantified results FIG. 2 shows the effect of BMP2 with S306E+N341T substitutions on chondrogenesis with or without presence of Noggin in chMM test; (A) shows Alcian blue stained cartilaginous extracellular matrix of mesenchymal precursor cells in the chick micromass; (B) shows quantified results FIG. 3 shows the effect of BMP2 with P318K+N341K substitutions on chondrogenesis with or without presence of Noggin in chMM test; (A) shows Alcian blue stained cartilaginous extracellular matrix of mesenchymal precursor cells in the chick micromass; (B) shows quantified results FIG. 4 shows the effect of BMP2 with N341T+N384YH substitutions on chondrogenesis with or without presence of Noggin in chMM test; (A) shows Alcian blue stained cartilaginous extracellular matrix of mesenchymal precursor cells in the chick micromass; (B) shows quantified results FIG. 5 shows the effect of BMP2 with N341 K+N384YH substitutions on chondrogenesis with or without presence of Noggin in chMM test; (A) shows Alcian blue stained cartilaginous extracellular matrix of mesenchymal precursor cells in the chick micromass; (B) shows quantified results FIG. 6 shows the effect of BMP2 with S306E+N341T+N384YH substitutions on chondrogenesis with or without presence of Noggin in chMM test; (A) shows Alcian blue stained cartilaginous extracellular matrix of mesenchymal precursor cells in the chick micromass; (B) shows quantified results FIG. 7 shows the effect of BMP2 with S306E substitution on chondrogenesis with or without presence of Noggin in chMM test; (A) shows Alcian blue stained cartilaginous extracellular matrix of mesenchymal precursor cells in the chick micromass; (B) shows quantified results FIG. 8 shows the effect of BMP2 with P318K substitution on chondrogenesis with or without presence of Noggin in chMM test; (A) shows Alcian blue stained cartilaginous extracellular matrix of mesenchymal precursor cells in the chick micromass; (B) shows quantified results FIG. 9 shows the effect of BMP2 with N341T substitution on chondrogenesis with or without presence of Noggin in chMM test; (A) shows Alcian blue stained cartilaginous extracellular matrix of mesenchymal precursor cells in the chick micromass; (B) shows quantified results FIG. 10 shows the effect of BMP2 with N341 K substitution on chondrogenesis with or without presence of Noggin in chMM test; (A) shows Alcian blue stained cartilaginous extracellular matrix of mesenchymal precursor cells in the chick micromass; (B) shows quantified results FIG. 11 shows the effect of BMP2 with V381T substitution on chondrogenesis with or without presence of Noggin in chMM test; (A) shows Alcian blue stained cartilaginous extracellular matrix of mesenchymal precursor cells in the chick micromass; (B) shows quantified results FIG. 12 shows a quantitative comparison of the effect of BMP2 variants with single substitutions (S306E, P318K, N341 T, N341 K, V381 T and N384YH) to effects of BMP2 variants with two or more substitutions (S306E+N341T, P318K+N341K, N341 T+N384YH, N341 K+N384YH, S306E+N341K+N384YH).

EXAMPLES

Materials and Methods

The structure of the BMP2-NOG complex has been modeled by alignment of the sequence of human BMP2 on the Protein Data Bank (PDB) coordinates of the BMP7 dimer within the NOG:BMP7 structure (PDB entry 1 M4U), which was solved by X-ray crystallography (Groppe J, Greenwald J, Wiater E, Rodriguez-Leon J, Economides A N, Kwiatkowski W, Affolter M, Vale W W, Belmonte J C, Choe S., 2002, Structural basis of BMP signaling inhibition by the cystine knot protein Noggin. Nature 12; 420(6916):636-42). The BMP2-BMPR1A-ACVR2 complex is already solved (PDB entry 2goo) (Allendorph G P, Vale W W, Choe S. 2006, Structure of the ternary signaling complex of a TGF-beta superfamily member. Proc Natl Acad Sci USA 16; 103(20): 7643-8). Images of the molecular structure were produced using the UCSF Chimera package. The Nog and type I and II receptor binding sites have been determined using PP_SITE (Gao Y, Lai L (2004) Structure-based method for analyzing protein-protein interfaces. J Mol Model 10:44-54).

For functional characterization of the BMP2 variants we used the chicken micromass culture system. The micromass culture system is an in vitro model for chondrogenesis and allows screening of the biological activity of BMP2 or BMP2 variants in the absence or presence of the BMP inhibitor Noggin. (Duprez D M, Coltey M, Amthor H, Brickell P M, T -continued N341K_rev
(SEQ ID NO. 27)
tgaacaatggcatgcttagtggagttcagatgatcagc N341T_fwd
(SEQ ID NO. 28)
gatcatctgaactccactcatgccattgttcag N341T_rev
(SEQ ID NO. 29)
gtctgaacaatggcatgagtagtggagttcagatga N384YH_fwd
(SEQ ID NO. 30)
gaatgaaaaggttgtattaaagtaccactatcaggacatggttgtggagg N384YH_rev
(SEQ ID NO. 31)
cctccacaaccatgtcctgatagtggtactttaatacaaccttttcattc The resulting vector containing the mutated human BMP2 was transformed into chemically competent E. coli Top10 cells and positive clones were selected via sequencing. Inserts were subcloned via ClaI into the avian specific retroviral vector RCASBP-A (Morgan B A, Fekete D M., 1996, Manipulating gene expression with replication-competent retroviruses. Methods Cell Biol. 1996; 51:185-218). The cds of chicken Noggin was first cloned into the shuttle vector pSLAX-13 using a NcoI-compatible 5' overhang and BamHI and subcloned via ClaI into the RCASBP-B to allow co-infection of BMP2 and Noggin in the same cells.

For viral production, chicken fibroblast cell line DF-1 was grown at 37° C. to 70 confluence and transfected with 3 μg RCAS construct and 10 μl ExGene 500 (Fermentas) according to manufacturers' instructions. Cells were passaged several times using DF-1 standard media (DMEM 1 g/l Glucose, w/o L-Gln; 10% FCS; 2 CS; 2 mM L-Gln, Pen/Strep) until 6 cell culture plates of 15 cm ∅ showed 100 confluence. Afterwards, the media was changed to DF-1 starvation media (DMEM 1 g/l Glucose, w/o L-Gln; 1% FCS; 0.2% CS; 2 mM L-Gln, Pen/Strep) leading to an accumulation of viral particles in the media. On 3 consecutive days, the supernatant containing the viral particles was harvested, frozen in liquid nitrogen and stored at −80° C. until further processing.

The frozen supernatants were thawed at 37° C. and filtered on ice through a 0.45 μm Durapore filter (Millipore). Subsequently, the virus particles were pelleted via ultrazentrifugation at 22000 rpm (Rotor SW-32, Beckman) for 3 h at 4° C. The supernatant was removed and the pellet resuspended in the remaining media on ice for 1 h by shaking. Finally, the virus was frozen in liquid nitrogen and stored at −80° C.

The virus titer was determined by seeding DF-1 cells in a 24 well culture dish plate at a density of $7.6 \times 10^4$ cells/well and growing to a confluence of 70-80%. The concentrated viral supernatant was diluted from $1 \times 10^{-3}$ to $1 \times 10^{-6}$ and the DF-1 cells were infected with 1 μl/well and 10 μl/well of the dilution, respectively. Cells infected by the RCAS virus were marked using a monoclonal antibody 3C2 and the Vectastain ABC Kit (Vector Laboratories Inc.) and the number of infectious units of the respective virus was determined.

Viruses were used to co-infect chicken micromass cultures with BMP2 or BMP2 variants with or without Noggin. Fertilized chicken eggs were obtained from Tierzucht Lohmann (Cuxhafen, Germany) and incubated at 37.5° C. in a humidified egg incubator for 4.5 days. Limb buds of Hamburger/Hamilton stage 24 were isolated and ectoderm was removed by incubation with dispase (3 mg/ml) in HBSS. Cells were isolated from the limb buds by digestion with 0.1% collagenase type Ia and 0.1% trypsin followed by filtration of the cell suspension through a 40 μm filter (BD Falcon). Micromass cultures were plated at a density of $2*10^5$ cells per 10 μl drop in the centre of a 24-well tissue culture plate. Infection directly prior to plating was performed by adding concentrated replication-competent avian sarcoma (RCAS) viral supernatants: RCASBP-A containing the cds of wild-type human BMP2 or BMP2 variants and RCASBP-B containing the cds of wild-type chicken Nog. The cells were allowed to attach for 2 hours in a humidified atmosphere of 5% $CO_2$ at 37° C. and then complemented with media (DMEM-F12, 10% FBS, 0.2% chicken serum, 4 mM L-Gln, Pen/Strep). The medium was replaced every 2 days. After 5 days micromass cultures were stained by incorporation of Alcian blue into the extracellular matrix production reflecting proteoglycan-rich cartilaginous matrix after fixation with Kahles Fixative (28.9% (v/v) Ethanol, 0.37% formaldehyde, 3.9% (v/v) acetic acid) and staining with 0.05% Alcian blue in 1 N HCl. Quantification of the staining was achieved by extraction with 6 M guanidine hydrochloride overnight at room temperature. Dye concentration was determined spectrophotometrically at OD 595 nm. To compare the results of different experiments, the value of wild-type hBMP2 without cotransfection with Noggin was normalised to 1 in each data set. The measured data of the different variants and the controls with and without Noggin were correlated with this value. For each condition 4 replicates were performed in parallel (Seemann P, Schwappacher R, Kjaer K W, Krakow D, Lehmann K, Dawson K, Stricker S, Pohl J, Ploger F, Staub E, Nickel J, Sebald W, Knaus P, Mundlos S. 2005, Activating and deactivating mutations in the receptor interaction site of GDF5 cause symphalangism or brachydactyly type A2., J Clin Invest.115(9): 2373-81).

Results

Analyzes of the predicted BMP2-NOG complex identified the following amino acid positions in BMP2 to be essential for the inhibition of BMP2 by NOG: D304, S306, N311, D312, V315, A316, P318, G319, D335, N341, S370, E376, V381, K383, N384. We performed in silico mutagenesis using the FoldX algorithm (Guerois R, Nielsen J E, Serrano L (2002) Predicting changes in the stability of proteins and protein complexes: a study of more than 1000 mutations. J Mol Biol 320:369-387) to identify amino acid substitutions of BMP2 that reduce the binding affinity of BMP2 to Nog, but at the same time affect the binding of BMP2 to its receptors only minimally. We came up with the following amino acid substitution at the positions mentioned above:

D304 (D22 of SEQ ID No. 1)

D304 is a possible interaction partner of R210 in NOG. These amino acid substitutions should prevent binding of the side chains. BMP7 has a serine at the homologous position and because NOG is able to bind to BMP7, it is proposed that D304S has only a minor influence on the BMP2-NOG complex. Theoretical analyzes of the predicted BMP2-NOG complex hint into the direction that amino acid substitutions to arginine or histidine are destabilizing the complex more than D304S. Thus, preferred substitutions are D304R/D304S/D304H.

S306 (S24 of SEQ ID No. 1)

S306 coordinates and orientates D304 and N311 within the BMP2-NOG model. All of the three side chains could interact with R210. Additionally, the loop 307-311 is stabilized by the coordinates of the side chains. This loop, especially W210, is important for the BMP2-BMPR1a interaction. Therefore, an alteration of this loop could interfere with the type 1 receptor binding. The homologous position in BMP7 is an arginine, which forms a hydrogen bond with Q318 of the BMP7:NOG complex. This interaction seems to be important for the BMP-NOG contact site. Because BMP2 has a proline at position 318 a similar interaction is not possible within the BMP2-NOG complex. All of the proposed amino acid substitutions should prevent any interaction of the BMP2 variant to NOG at this position. Thus preferred substitutions are S306G/S306H/S306E.

N311 (N29 of SEQ ID No. 1)

N311 is, like D304 and S306, in proximity to R210. A mutation to threonine should prevent the interaction to Nog, but will keep the necessary orientation of W310, which is important for the interaction of BMP2 with BMPR1A, because of a hydrogen bonding to S306. Thus, a preferred substitution is N311T.

D312 (D30 of SEQ ID No. 1)

D312 might interact with Q208 of NOG. A substitution to alanine or threonine should prevent this interaction. Thus, preferred substitutions are D312A/D312T.

V315 (V33 of SEQ ID No. 1)

V315 together with L372 and A316 build a hydrophobic contact side to NOG and ACVR2. A mutation to arginine should allow binding to the type 2 receptor, but prevents NOG binding. Arginine will interact with T63 of ACVR2, but R204 of NOG will lead to steric hindrance. Thus, a preferred substitution is V315R.

A316 (A34 of SEQ ID No. 1)

A316 together with L372, V315, P317, P318 and L382 build a hydrophobic contact site to L46 of NOG and W79 of ACVR2. An amino acid substitution of A316 to tyrosine or aspartate should have a negative effect on the BMP2 interaction with NOG or ACVR2, but A316Y should be less dramatic than the A316D mutation. Thus, preferred substitutions are A316Y/A316D.

P318 (P36 of SEQ ID No. 1)

P318 together with P317 are important residues for the main peptide chain, especially for the bending to the contact site of ACVR2 and NOG. Every amino acid substitution at this site should have a negative effect on NOG and receptor type 2 binding. Substitutions to lysine, arginine or serine should have the strongest negative effects. Thus, preferred substitutions are P318K/P318R/P318S.

G319 (G37 of SEQ ID No. 1)

G319 is important for the bending of the main chain towards its curved contact site. A mutation to threonine could interfere with the bending of the main chain and therefore influence indirectly the BMP2 interaction with receptor type 2 or NOG in a negative way. A direct influence is not possible, because the side chain points into the opposite direction of the receptor. Thus, a preferred substitution is G319T.

D335 (D53 of SEQ ID No. 1)

The side chain of D335 has a direct contact towards the main chain of NOG with M27 and Y30 of the N-terminal end of NOG. D355 builds a hydrogen bond towards T78 of BMPR1A. An amino acid substitution to tyrosine should influence the interaction to NOG more efficiently than to BMPR1A. Thus, a preferred substitution is D335Y.

N341 (N59 of SEQ ID No. 1)

N341 is important for the BMP2 dimer stabilization and the contact site of BMPR1A. N341 orientates den N-terminal end of NOG via a double hydrogen bond towards the main chain. This interaction is prevented by an amino substitution to lysine or threonine. The destabilizing effect should influence the binding to NOG more than the binding to BMPR1A. Thus, preferred substitutions are N341K/N341T/N341V/N341E.

S370 (S88 of SEQ ID No. 1)

S370 builds a hydrogen bond to the main chain L80 of ACVR2 or V44 of NOG. In addition, it coordinates S370 the side chain of N384 and is involved in the alignment of the N-terminal arm of NOG. An amino acid substitution to alanine shouldn't influence the ACVR2 interaction, because it is compatible with the hydrophobic interaction. On the other hand, the alanine-substitution might influence the alignment of the N-terminal arm of NOG and therefore interfere with the BMP2-NOG binding. Thus, a preferred substitution is S370A.

E376 (E94 of SEQ ID No. 1)

E376 might build a hydrogen bond with R34 and Q28 of NOG, which stabilizes the N-terminal arm of NOG. E376 might also build hydrogen bonds with K111 and R126 of BMPR1A (which was not seen in BMP2-RI/RII model). Therefore, it is proposed that an amino acid substitution to proline has only a minor effect on the BMPR1A interaction, but at the same time interfering with the loop of the main chain (374-377) and thereby destabilizing the N-terminal arm of NOG. Thus, a preferred substitution is E376P.

V381 (V99 of SEQ ID No. 1)

The side chain of V381 interacts only within the BMP2 monomer. But its main chain is in an optimal position for a beta-beta main chain interaction with NOG. Therefore, it is proposed that an amino acid substitution to threonine or tyrosine should interfere with the geometry of the main chain weakening the NOG interaction of BMP2. Thus, preferred substitutions are V381T/V381Y.

K383 (K101 of SEQ ID No. 1)

K383 could indirectly influence the orientation and binding of N341 (BMP2) and E104 (RI). K383 has a side chain interaction with D39 and therefore influences the N-terminal arm of NOG. A mutation to isoleucine or leucine should prevent this interaction without influencing the BMPR1A interaction. Thus, preferred substitutions are K383I/K383L.

N384 (N102 of SEQ ID No. 1)

The N-terminal arm of NOG covers N384. BMP9 has an additional amino acid here so that the clipping of the N-terminal arm of NOG is disabled. It is proposed that this is one of the main reasons that BMP9 is not inhibited by NOG. Therefore, we introduced a tyrosine and a histidine analogue of the BMP9 sequence into BMP2. An amino acid substitution to serine, valine or thryptophane prevents hydrogen bonding to NOG and should therefore also interfere with the BMP2-NOG binding. Thus, preferred substitutions are N384YH/N384S/N384V/N384W.

NOG has a large contact site in BMPs, because it needs to blocks both pairs of receptor binding sites in order to inhibit BMP activity.

We propose that the influence of single amino acid substitution are only marginal and that one needs to combine 2 or more of the amino acid substitutions at the same time to obtain BMP2 variants with a profound Noggin insensitivity.

A proof of concept was achieved using the chicken limb bud micromass system to analyse the functional abilities of the hBMP2 variants to induce cartilage production in a well defined in vitro system (FIGS. 1-12). By incorporation of Alcian blue into the extracellular matrix the production of proteoglycan-rich cartilaginous matrix is determined. The chondrogenic differentiation of the mesenchymal precursor cells in the chicken micromass can hereby be both visualised and quantified. Hence the potential of the hBMP2 variants to induce chondrogenesis is efficiently tested. Micromass cultures were retrovirally infected with a hBMP2-expressing virus to express the wild-type protein or its variants. Simultaneously, Noggin was co-expressed in the cells when the variants were tested for their sensitivity towards the antagonist. After 5 days of cultivation the chicken micromass cultures were stained with Alcian blue.

As expected, infection of micromass cells with wild-type hBMP2 led to a massive induction of cartilage production compared to the non-infected control cells. However, the wild-type was completely blocked when Noggin was co-expressed.

Like the wild-type, all variants were able to induce chondrogenesis efficiently in the absence of Noggin. The only exception is the variant containing the substitution N384YH which exhibited no induction of chondrogenesis and is comparable to the control. Furthermore, none of the single mutations was able to induce Noggin resistance apart from the variant with the substitution P318K. This point mutation led to some resistance against the antagonist.

However, the combination of two or three single mutations resulted in a significant increase in Noggin resistance. This could be observed especially in the variants N341T+N384YH, N341K+N384YH and P318K+N341K. When they were coexpressed with Noggin, their chondrogenic potential ranged from 50% to 75% of the wild-type activity in the absence of its antagonist. The variants containing the substitutions S306E+N341T and S306E+N341K+N384YH resulted in Noggin resistance comparable to the single mutation P318K. They exhibited around one third of the activity observed in the single transfection with the wild-type.

In conclusion, it is shown that the combination of two or three specific point mutations increases the Noggin resistance of hBMP2 significantly, leading to strong chondrogenic effects even in the presence of its main antagonist.

The invention claimed is:

1. An isolated peptide having BMP-2 activity comprising an amino acid sequence having at least 90% sequence identity with SEQ ID No. 1, wherein said amino acid sequence comprises at least a first and second amino acid substitution, wherein the first amino acid substitution occurs at a position corresponding to N59, E94, V99, K101 or N102 of SEQ ID No. 1.

2. The isolated peptide of claim 1, wherein the first amino acid substitution is selected from the group of N59K, N59T, N59V, N59E, E94P, V99T, V99Y, K101I, K101L, N102S, N102V, N102W and N102YH.

3. The isolated peptide of claim 1, wherein the second amino acid substitution occurs at a position corresponding to D22, S24, V26, N29, D30, V33, A34, P36, G37, H39, F41, H44, P48, A52, D53, L55, N59, E94, V99, K101 or N102 of SEQ ID No. 1.

4. The isolated peptide of claim 3, wherein the second amino acid substitution is selected from the group of D22R, D22S, D22H, S24G, S24H, S24E, S24Q, V26L, N29T, N29Q, D30A, D30T, V33I, V33R, A34Y, A34D, P36K, P36R, P36S, G37T, H39A, F41 N, H44D, P48S, A52N, D53A, D53Y, L55M, N59K, N59T, N59V, N59E, S88A, E94P, V99T, V99Y, K101I, K101L, N102S, N102V, N102W and N102YH.

5. The isolated peptide of claim 3, wherein the second amino acid substitution occurs at a position corresponding to D22, S24, N29, D30, V33, A34, P36, G37, D53, N59, S88, E94, V99, K101 or N102 of SEQ ID No. 1.

6. The isolated peptide of claim 3, wherein the second amino acid substitution is selected from the group of D22R, D22S, D22H, S24G, S24H, S24E, N29T, D30A, D30T, V33R, A34Y, A34D, P36K, P36R, P36S, G37T, D53Y, N59K, N59T, N59V, N59E, S88A, E94P, V99T, V99Y, K101I, K101L, N102S, N102V, N102W and N 102YH.

7. The isolated peptide of claim 5, wherein said amino acid sequence comprises further amino acid substitutions.

8. The isolated peptide of claim 1, wherein the isolated peptide comprises an amino acid sequence having at least 90% sequence identity with SEQ ID No. 11.

9. An isolated nucleic acid, wherein said isolated nucleic acid comprises:
i) a nucleic acid sequence encoding the peptide of claim 1.

10. A transformed or transfected cell expressing an isolated peptide comprising an amino acid sequence having at least 90% sequence identity with SEQ ID No. 1, wherein said amino acid sequence comprises at least a first and a second amino acid substitution, wherein the first amino acid substitution occurs at a position corresponding to N59, E94, V99, K101 or N102 of SEQ ID No. 1 and wherein said organism or cell comprises an isolated nucleic acid of claim 9.

11. A method for treating BMP-related diseases or conditions comprising
administering to a subject in need thereof an effective dose of an isolated peptide having BMP-2 activity, wherein said peptide comprises an amino acid sequence having at least 90% sequence identity with SEQ ID No. 1, wherein said amino acid sequence comprises at least a first and a second amino acid substitution, wherein the first amino acid substitution occurs at a position corresponding to N59, E94, V99, K101 or N102 of SEQ ID No. 1.

12. A pharmaceutical composition comprising a peptide having BMP-2 activity comprising an amino acid sequence having at least 90% sequence identity with SEQ ID No. 1, wherein said amino acid sequence comprises at least a first and a second amino acid substitution, wherein the first amino acid substitution occurs at a position corresponding to N59, E94, V99, K101 or N102 of SEQ ID No. 1 and at least one pharmaceutically acceptable excipient.

13. A method for manufacturing a medicament comprising providing a peptide having BMP-2 activity comprising an amino acid sequence having at least 90% sequence identity with SEQ ID No. 1, wherein said amino acid sequence comprises at least a first and second amino acid substitution, wherein the first amino acid substitution occurs at a position corresponding to N59, E94, V99, K101 or N102 of SEQ ID No. 1 and manufacturing said medicament.

14. An isolated peptide having BMP-2 activity comprising an amino acid sequence having at least 90% sequence identity with SEQ ID No. 1, wherein said amino acid sequence comprises at least a first and a second amino acid substitution, wherein said first amino acid substitution occurs at a position corresponding to N59 of SEQ ID No. 1.

15. The isolated peptide of claim 1, wherein the peptide consists of said amino acid sequence.

16. The isolated peptide of claim 14, wherein the peptide consists of said amino acid sequence.

17. The isolated peptide of claim 7, wherein the peptide comprises three or four amino acid substitutions.

18. The isolated peptide of claim 14, wherein said first amino acid substitution is N59V and said second amino acid substitution is N102W.

19. The method of claim 11,
wherein treating such diseases or conditions comprises:
formation of bone, cartilage, non-mineralized skeletal or connective tissue,
increase of bone mass in metabolic bone disease,
replacement or repair of bone and/or cartilage at injury sites, or
periodontal tissue regeneration.

20. The method of claim 11,
wherein treating such diseases or conditions comprises:
liver regeneration,
enhancement of functional recovery following central nervous system ischemia or trauma,
dendritic growth, or
neural cell adhesion.

21. The method of claim 11,
wherein such diseases or conditions are:
metabolic bone diseases,
breaks, fractures and/or tears of bone and/or cartilage at injury sites,
chronic renal failure, or
Parkinson's disease.

22. The method of claim 19, wherein the treating comprises formation of bone, cartilage, non-mineralized skeletal or connective tissue, increase of bone mass in metabolic bone disease, replacement or repair of bone and/or cartilage at injury sites or periodontal tissue regeneration.

23. A method for transfecting or transforming a host cell comprising introducing the nucleic acid of claim 9 into said host cell.

* * * * *